United States Patent [19]
Brenner

[11] Patent Number: 5,635,400
[45] Date of Patent: Jun. 3, 1997

[54] MINIMALLY CROSS-HYBRIDIZING SETS OF OLIGONUCLEOTIDE TAGS

[75] Inventor: Sydney Brenner, Cambridge, England

[73] Assignee: Spectragen, Inc., Hayward, Calif.

[21] Appl. No.: 478,238

[22] Filed: Jun. 7, 1995

Related U.S. Application Data

[63] Continuation of Ser. No. 358,810, Dec. 19, 1994, which is a continuation-in-part of Ser. No. 322,348, Oct. 13, 1994, abandoned.

[51] Int. Cl.$^6$ .............................. C12N 15/09; C12Q 1/68; C07H 21/00
[52] U.S. Cl. ..................... 435/320.1; 435/6; 435/172.3; 536/22.1; 536/24.2
[58] Field of Search .................... 435/6, 172.3, 320.1; 536/24.2, 22.1

[56] References Cited

U.S. PATENT DOCUMENTS

| | | | |
|---|---|---|---|
| 5,302,509 | 4/1994 | Cheeseman | 435/6 |
| 5,482,836 | 1/1996 | Cantor et al. | 435/6 |

FOREIGN PATENT DOCUMENTS

| | | |
|---|---|---|
| 2036946 | 10/1991 | Canada . |
| 0 303 459 A3 | 2/1989 | European Pat. Off. . |
| 90107066 | 10/1990 | European Pat. Off. . |
| WO90/03382 | 4/1990 | WIPO . |
| WO92/00091 | 1/1992 | WIPO . |
| WO92/10588 | 6/1992 | WIPO . |
| WO92/10587 | 6/1992 | WIPO . |
| WO93/06121 | 4/1993 | WIPO . |
| 93/17126 | 9/1993 | WIPO . |
| WO93/21203 | 10/1993 | WIPO . |
| WO93/22684 | 11/1993 | WIPO . |
| WO93/22680 | 11/1993 | WIPO . |
| WO94/08051 | 4/1994 | WIPO . |
| WO95/20053 | 7/1995 | WIPO . |

OTHER PUBLICATIONS

Brenner et al., "Encoded combinatorial chemistry", Proc. Natl. Acad. Sci. USA 89:5381–5383 Jun. 1992.
Church et al., "Multiplex DNA sequencing", Science 240: 185–188 Apr. 8, 1988.
Crick et al, "Codes without commas," Proc. Natl. Acad. Sci., 43: 416–421 (1957).
Ohlmeyer et al, "Complex synthetic chemical libraries indexed with molecular tags," Proc. Natl. Acad. Sci., 90: 10922–10926 (1993).
Maskos and Southern, "Oligonucleotide hybridizations on glass supports: a novel linker for oligonucleotide synthesis and hybridization properties of oligonucleotides synthesized in situ," Nucleic Acids Research, 20: 16/9–1684 (1992).
Matthews and Kricka, "Analytical strategies for the use of DNA probes," Anal. Biochem. 169: 1–25 (1988).
Broude et al, "Enhanced DNA sequencing by hybridization," Proc. Natl. Acad Sci, 91 3072–3076 (1994).
Nielsen et al, "Synthetic methods for the implementation of encoded combinatorial chemistry," J. Am. Chem. Soc. 115; 9812–9813 (1993).
Needels et al, "Generation and screening ot an oligonucleotide–encoded synthetic peptide library," Proc. Natl. Acad. Sci., 90: 10700–10704 (1993).
Chetverin et al, "Oligonucleotide arrays: New concepts and possibilities," Biotechnology, 12: 1093–1099 (1994).
Yang and Youvan, "A prospectus for multispectral–multiplex DNA sequencing," Biotechnology, 7: 576–580 (1989).
Beck et al, "A strategy for the amplification, purification, and selection of M13 templates for large–scale DNA sequencing," Analytical Biochemistry, 212: 498–505 (1993).
Ji and Smith, "Rapid purification of double–stranded DNA by triple–helix–mediated affinity capture," Anal. Chem., 65: 1323–1328 (1993).
Brown et al, "A new base-stable linker for solid–phase oligonucleotide synthesis," J. Chem. Soc. Commun. 1989: 891–893.
Oliphant et al, "Cloning of random–sequence oligodeoxynucleotides," Gene, 44: 177–183 (1986).
Hunkapiller et al, "Large–scale and automated DNA sequence determination," Science, 254: 59–67 (1991).
Coche et al, "Reducing bias in cDNA sequence representation by molecular selection," Nucleic Acids Research, 22: 4545–4546 (1994).
Kuijper et al, "Functional cloning vectors for use in directional cDNA cloning using cohesive ends produced with T4 DNA polymerase," Gene, 112: 147–155 (1992).
Aslanidis et al, "Ligation–independent cloning of PCR products (LIC–PCR)," Nucleic Acids Research, 18: 6069–6074 (1990).
Wetmur, "DNA probes: applications of the principles of nucleic acid hybridization," Critical Reviews in Biochemistry and Molecular Biology, 26: 227–259 (1991).
Egholm et al, "PNA hybridizes to complementary oligonucleotides obeying the Watson–Crick hydrogen–bonding rules," Nature, 365: 566–568 (1993).
Gryaznov et al, "Modulation of oligonucleotide duplex and triplex stabillity via hydrophobic interactions," Nucleic Acids Research, 21: 5909–5915 (1993).

*Primary Examiner*—George C. Elliott
*Assistant Examiner*—Scott D. Priebe
*Attorney, Agent, or Firm*—Stephen C. Macevicz

[57] ABSTRACT

The invention provides a method of tracking, identifying, and/or sorting classes or subpopulations of molecules by the use of oligonucleotide tags. Oligonucleotide tags of the invention each consist of a plurality of subunits 3 to 6 nucleotides in length selected from a minimally cross-hybridizing set. A subunit of a minimally cross-hybridizing set forms a duplex or triplex having two or more mismatches with the complement of any other subunit of the same set. The number of oligonucleotide tags available in a particular embodiment depends on the number of subunits per tag and on the length of the subunit. An important aspect of the invention is the use of the oligonucleotide tags for sorting polynucleotides by specifically hybridizing tags attached to the polynucleotides to their complements on solid phase supports. This embodiment provides a readily automated system for manipulating and sorting polynucleotides, particularly useful in large-scale parallel operations, such as large-scale DNA sequencing, mRNA fingerprinting, and the like, wherein many target polynucleotides or many segments of a single target polynucleotide are sequenced simultaneously.

4 Claims, 6 Drawing Sheets

MINIMALLY CROSS-HYBRIDIZING SETS OF OLIGONUCLEOTIDE TAGS

This is a continuation of co-pending U.S. patent application Ser. No. 08/358,810 filed 19 Dec. 1994, which is a continuation-in-part of U.S. patent application Ser. No. 08/322,348 filed 13 Oct. 1994 now abandoned, which application is incorporated by reference.

FIELD OF THE INVENTION

The invention relates generally to methods for identifying, sorting, and/or tracking molecules, especially polynucleotides, with oligonucleotide labels, and more particularly, to a method of sorting polynucleotides by specific hybridization to oligonucleotide tags.

BACKGROUND

Specific hybridization of oligonucleotides and their analogs is a fundamental process that is employed in a wide variety of research, medical, and industrial applications, including the identification of disease-related polynucleotides in diagnostic assays, screening for clones of novel target polynucleotides, identification of specific polynucleotides in blots of mixtures of polynucleotides, amplification of specific target polynucleotides, therapeutic blocking of inappropriately expressed genes, DNA sequencing, and the like, e.g. Sambrook et al., Molecular Cloning: A Laboratory Manual, 2nd Edition (Cold Spring Harbor Laboratory, New York, 1989); Keller and Manak, DNA Probes, 2nd Edition (Stockton Press, New York, 1993); Milligan et al., J. Med. Chem., 36: 1923–1937 (1993); Drmanac et al., Science, 260:1649–1652 (1993); Bahas, J. DNA Sequencing and Mapping, 4:143–150 (1993).

Specific hybridization has also been proposed as a method of tracking, retrieving, and identifying compounds labeled with oligonucleotide tags. For example, in multiplex DNA sequencing oligonucleotide tags are used to identify electrophoretically separated bands on a gel that consist of DNA fragments generated in the same sequencing reaction. In this way, DNA fragments from many sequencing reactions are separated on the same lane of a gel which is then blotted with separate solid phase materials on which the fragment bands from the separate sequencing reactions are visualized with oligonucleotide probes that specifically hybridize to complementary tags, Church et al., Science, 240:185–188 (1988). Similar uses of oligonucleotide tags have also been proposed for identifying explosives, potential pollutants, such as crude oil, and currency for prevention and detection of counterfeiting, e.g. reviewed by Dollinger, Pages 265–274 in Mullis et al., editors, The Polymerase Chain Reaction (Birkhauser, Boston, 1994). More recently, systems employing oligonucleotide tags have also been proposed as a means of manipulating and identifying individual molecules in complex combinatorial chemical libraries, for example, as an aid to screening such libraries for drug candidates, Brenner and Lerner, Proc. Natl. Acad. Sci., 89:5381–5383 (1992); Alper, Science, 264:1399–1401 (1994); and Needels et al., Proc. Natl. Acad. Sci., 90:10700–10704 (1993).

The successful implementation of such tagging schemes depends in large part on the success in achieving specific hybridization between a tag and its complementary probe. That is, for an oligonucleotide tag to successfully identify a substance, the number of false positive and false negative signals must be minimized. Unfortunately, such spurious signals are not uncommon because base pairing and base stacking free energies vary widely among nucleotides in a duplex or triplex structure. For example, a duplex consisting era repeated sequence of deoxyadenine (A) and thyroidinc (T) bound to its complement may have less stability than an equal-length duplex consisting of a repeated sequence of deoxyadenine (G) and deoxycytidine (C) bound to a partially complementary target containing a mismatch. Thus, if a desired compound from a large combinatorial chemical library were tagged with the former oligonucleotide, a significant possibility would exist that, under hybridization conditions designed to detect perfectly matched AT-rich duplexes, undesired compounds labeled with the GC-rich oligonucleotide—even in a mismatched duplex—would be detected along with the perfectly matched duplexes consisting of the AT-rich tag. In the molecular tagging system proposed by Brenner et al. (cited above), the related problem of mis-hybridizations of closely related tags was addressed by employing a so-called "commaless" code, which ensures that a probe out of register (or frame shifted) with respect to its complementary tag would result in a duplex with one or more mismatches for each of its five or more three-base words, or "condons."

Even though reagents, such as tetramethylammonium chloride, are available to negate base-specific stability differences of oligonucleotide duplexes, the effect of such reagents is often limited and their presence can be incompatible with, or render more difficult, further manipulations of the selected compounds, e.g. amplification by polymerase chain reaction (PCR), or the like.

Such problems have made the simultaneous use of multiple hybridization probes in the analysis of multiple or complex genetic loci, e.g. via multiplex PCR, reverse dot blotting or the like, very difficult. As a result, direct sequencing of certain loci, e.g. HLA genes, has been promoted as a reliable alternative to indirected methods employing specific hybridization for the identification of genotypes, e.g. Gyllensten et al., Proc. Natl. Acad. Sci., 85:7652–7656 (1988).

The ability to sort cloned and identically tagged DNA fragments onto distinct solid phase supports would facilitate such sequencing, particularly when coupled with a non gel-based sequencing methodology simultaneously applicable to many samples in parallel.

In view of the above, it would be useful if there were available an oligonucleotide-based tagging system which provided a large repertoire of tags, but which also minimized the occurance of false positive and false negative signals without the need to employ special reagents for altering natural base pairing and base stacking free energy differences. Such a tagging system would find applications in many areas, including construction and use of combinatorial chemical libraries, large-scale mapping and sequencing of DNA, genetic identification, medical diagnostics, and the like.

SUMMARY OF THE INVENTION

An object of my invention is to provide a molecular tagging system for tracking, retrieving, and identifying compounds.

Another object of my invention is to provide a method for sorting identical molecules, or subclasses of molecules, especially polynucleotides, onto surfaces of solid phase materials by the specific hybridization of oligonucleotide tags and their complements.

A further object of my invention is to provide a combinatorial chemical library whose member compounds are identified by the specific hybridization of oligonucleotide tags and their complements.

A still further object of my invention is to provide a system for tagging and sorting many thousands of fragments, especially randomly overlapping fragments, of a target polynucleotide for simultaneous analysis and/or sequencing.

Another object of my invention is to provide a rapid and reliable method for sequencing target polynucleotides having a length in the range of a few hundred basepairs to several tens of thousands of basepairs.

My invention achieves these and other objects by providing a method and materials for tracking, identifying, and/or sorting classes or subpopulations of molecules by the use of oligonucleotide tags. An oligonucleotide tag of the invention consists of a plurality of subunits, each subunit consisting of an oligonucleotide of 3 to 6 nucleotides in length. Subunits of an oligonucleotide tag are selected from a minimally cross-hybridizing set. In such a set, a duplex or triplex consisting of a subunit of the set and the complement of any other subunit of the set contains at least two mismatches. In other words, a subunit of a minimally cross-hybridizing set at best forms a duplex or triplex having two mismatches with the complement of any other subunit of the same set. The number of oligonucleotide tags available in a particular embodiment depends on the number of subunits per tag and on the length of the subunit. The number is generally much less than the number of all possible sequences the length of the tag which for a tag n nucleotides long would be $4^n$. More preferably, subunits are oligonucleotides from 4 to 5 nucleotides in length.

In one aspect of my invention, complements of oligonucleotide tags attached to a solid phase support are used to sort polynucleotides from a mixture of polynucleotides each containing a tag. In this embodiment, complements of the oligonucleotide tags are synthesized on the surface of a solid phase support, such as a microscopic bead or a specific location on an array of synthesis locations on a single support, such that populations of identical sequences are produced in specific regions. That is, the surface of each support, in the case of a bead, or of each region, in the case of an array, is derivatized by only one type of complement which has a particular sequence. The population of such beads or regions contains a repertoire of complements with distinct sequences, the size of the repertoire depending on the number of subunits per oligonucleotide tag and the length of the subunits employed. Similarly, the polynucleotides to be sorted each comprises an oligonucleotide tag in the repertoire, such that identical polynucleotides have the same tag and different polynucleotides have different tags. Thus, when the populations of supports and polynucleotides are mixed under conditions which permit specific hybridization of the oligonucleotide tags with their respective complements, subpopulations of identical polynucleotides are sorted onto particular beads or regions. The subpopulations of polynucleotides can then be manipulated on the solid phase support by micro-biochemical techniques.

Generally, the method of my invention comprises the following steps: (a) attaching an oligonucleotide tag from a repertoire of tags to each molecule in a population of molecules (i) such that substantially all the same molecules or same subpopulation of molecules in the population have the same oligonucleotide tag attached and substantially all different molecules or different subpopulations of molecules in the population have different oligonucleotide tags attached and (ii) such that each oligonucleotide tag from the repertoire comprises a plurality of subunits and each subunit of the plurality consists of an oligonucleotide having a length from three to six nucleotides or from three to six basepairs, the subunits being selected from a minimally cross-hybridizing set; and (b) sorting the molecules or subpopulations of molecules of the population by specifically hybridizing the oligonucleotide tags with their respective complements.

An important aspect of my invention is the use of the oligonucleotide tags to sort polynucleotides for parallel sequence determination. Preferably, such sequencing is carded out by the following steps: (a) generating from the target polynucleotide a plurality of fragments that cover the target polynucleotide; Co) attaching an oligonucleotide tag from a repertoire of tags to each fragment of the plurality (i) such that substantially all the same fragments have the same oligonucleotide tag attached and substantially all different fragments have different oligonucleotide tags attached and (ii) such that each oligonucleotide tag from the repertoire comprises a plurality of subunits and each subunit of the plurality consists of an oligonucleotide having a length from three to six nucleotides or from three to six basepairs, the subunits being selected from a minimally crosshybridizing set;

sorting the fragments by specifically hybridizing the oligonucleotide tags with their respective complements; (c) determining the nucleotide sequence of a portion of each of the fragments of the plurality, preferably by a single-base sequencing methodology as described below; and (d) determining the nucleotide sequence of the target polynucleotide by collating the sequences of the fragments.

My invention overcomes a key deficiency of current methods of tagging or labeling molecules with oligonucleotides: By coding the sequences of the tags in accordance with the invention, the stability of any mismatched duplex or triplex between a tag and a complement to another tag is far lower than that of any perfectly matched duplex between the tag and its own complement. Thus, the problem of incorrect sorting because of mismatch duplexes of GC-rich tags being more stable than perfectly matched AT-rich tags is eliminated.

When used in combination with solid phase supports, such as microscopic beads, my invention provides a readily automated system for manipulating and sorting polynucleotides, particularly useful in large-scale parallel operations, such as large-scale DNA sequencing, wherein many target polynucleotides or many segments of a single target polynucleotide are sequenced and/or analyzed simultaneously.

DEFINITIONS

Figure 1A:
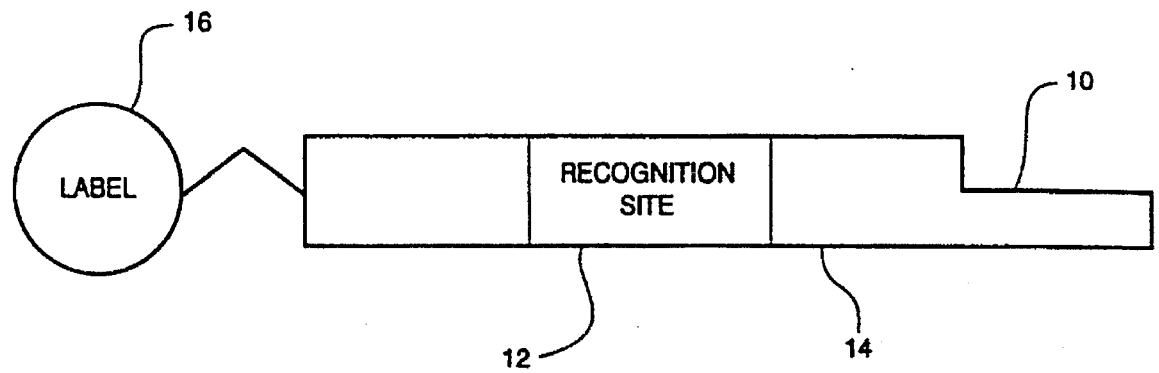
FIGS. 1a–1c illustrates structures of labeled probes employed in a preferred method of "single base" sequencing which may be used with the invention.
Figure 2:
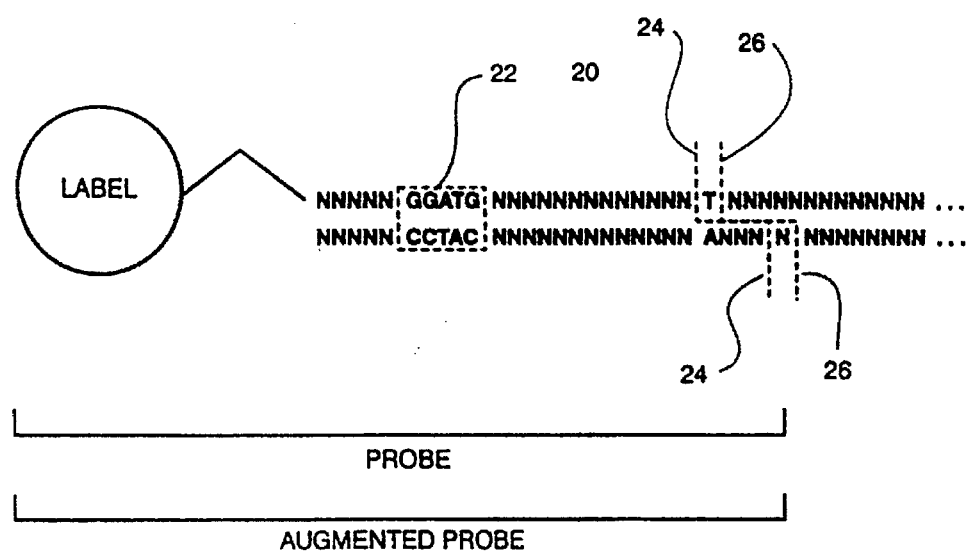
FIG. 2 illustrates the relative positions of the nuclease recognition site, ligation site, and cleavage site in a (SEQ ID NO: 16) formed between a target polynucleotide and a probe used in a preferred "single base" sequencing method.
Figure 1B:
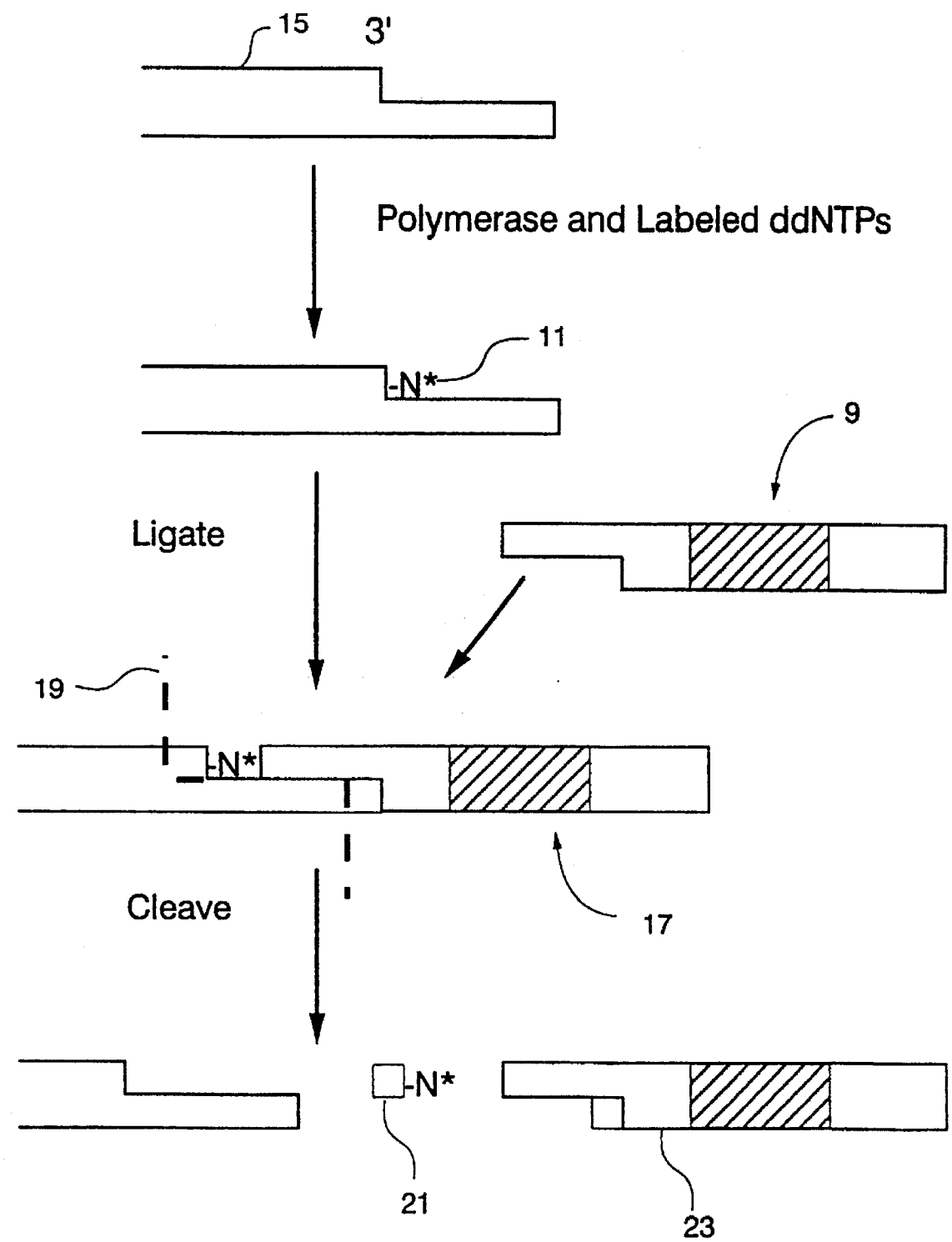

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified toohomers or linkages, including deoxyribonucleosides, ribonucleosides, α-anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually toohomers are linked by phosphortester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'→3' order from left to fight and that "A" denotes deoxyadenosine, "C" denotes deoxycytidine, "G" denotes deoxyguanosine, and "T" denotes thyroidinc, unless otherwise noted. Analogs of phosphodiester linkages include phosphorothioate, phosphorodithioate, phosphoranilidate, phosphoramidate, and the like. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Komberg and Baker, DNA Replication, 2nd led. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90:543–584 (1990), or the like, with the only proviso that they are capable of specific hybridization. Such analogs include synthetic nucleosides designed to enhance binding properties, reduce degeneracy, increase specificity, and the like.

DETAILED DESCRIPTION OF THE INVENTION

The invention provides a method of labeling and sorting molecules, particularly polynucleotides, by the use of oligonucleotide tags. The oligonucleotide tags of the invention comprise a plurality of "words" or subunits selected from minimally cross-hybridizing sets of subunits. Subunits of such sets cannot form a duplex or triplex with the complement of another subunit of the same set with less than two mismatched nucleotides. Thus, the sequences of any two oligonucleotide tags of a repertoire that form duplexes will never be "closer" than differing by two nucleotides. In particular embodiments, sequences of any two oligoncule-otide tags of a repertoire can be even "further" apart, e.g. by designing a minimally cross-hybridizing set such that subunits cannot form a duplex with the complement of another subunit of the same set with less than three mismatched nucleotides, and so on. The invention is particularly useful in labeling and sorting polynucleotides for parallel operations, such as sequencing, fingerprinting or other types of analysis.

Figure 3:
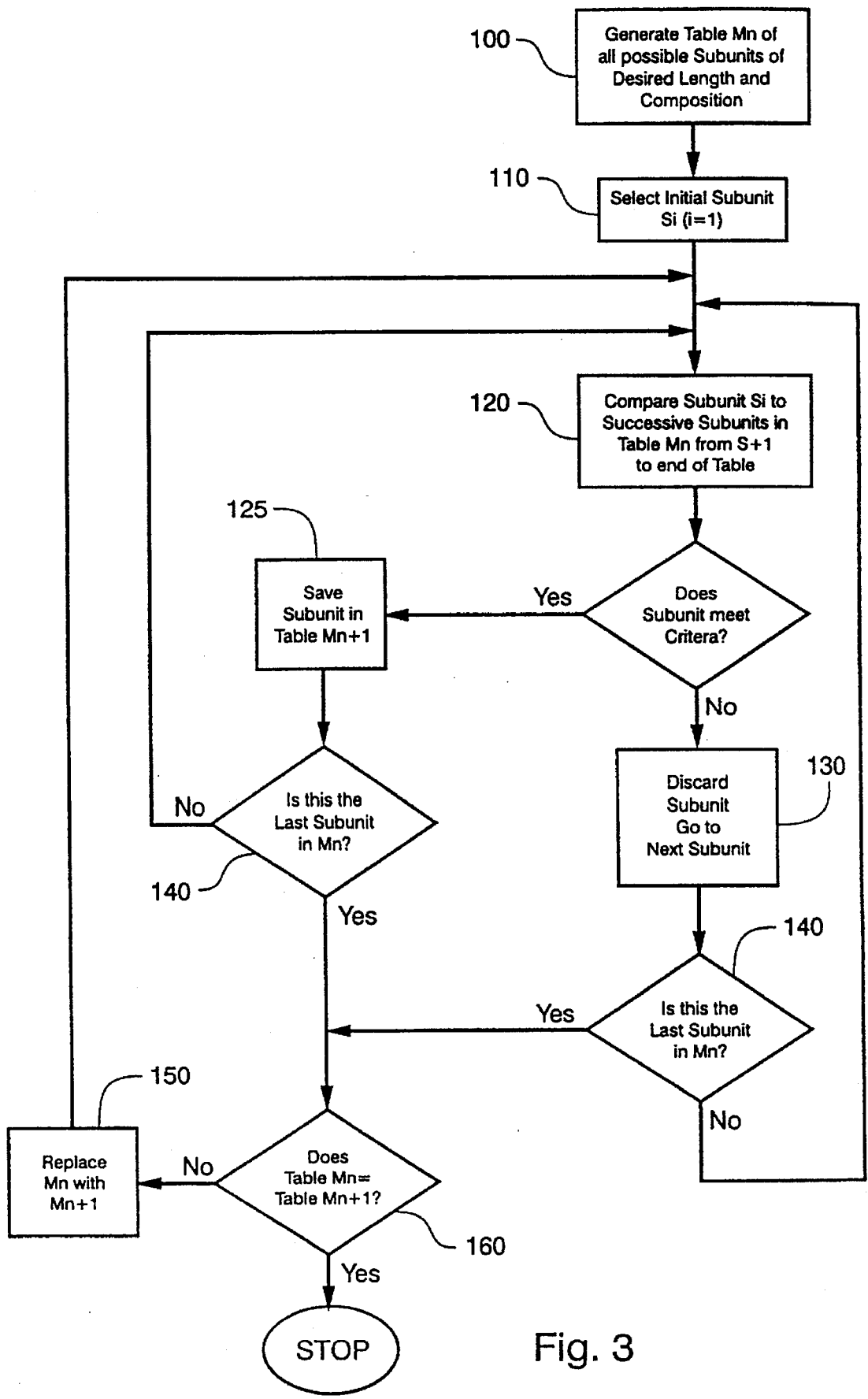
FIG. 3 is a flow chart illustrating a general algorithm for generating minimally cross-hybridizing sets.
Figure 1C:
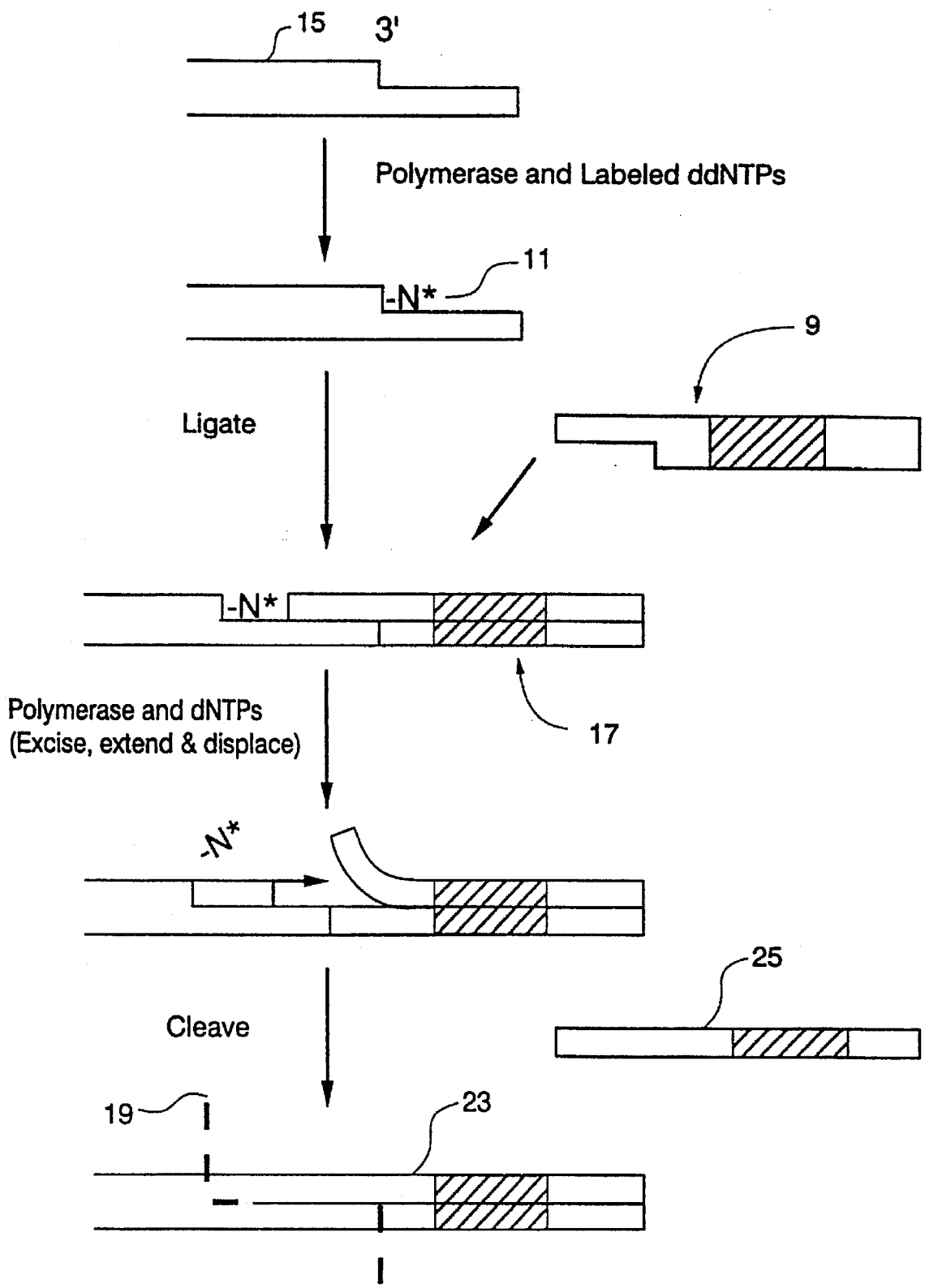

Constructing Oligonucleotide Tags from Minimally Cross-Hybridizing Sets of Subunits The nucleotide sequences of the subunits for any minimally crosshybridizing set are conveniently enumerated by simple computer programs following the general algorithm illustrated in FIG. 3, and as exemplified by program minhx whose source code is listed in Appendix I. Minhx computes all minimally cross-hybridizing sets having subunits composed of three kinds of nucleotides and having length of four.

The algorithm of FIG. 3 is implemented by first defining the characteristic of the subunits of the minimally cross-hybridizing set, i.e. length, number of base differences between members, and composition, e.g. do they consist of two, three,, or four kinds of bases. A table $M_n$, n–1, is generated (100) that consists of all possible sequences of a given length and composition. An initial subunit $S_1$ is selected and compared (120) with successive subunits $S_i$ for i=n+1 to the end of the table. Whenever a successive subunit has the required number of mismatches to be a member of the minimally cross-hybridizing set, it is saved in a new table $M_{n+1}$ (125), that also contains subunits previously selected in prior passes through step 120. For example, in the first set of comparisons, $M_2$ will contain $S_1$; in the second set of comparisons, $M_3$ will contain $S_1$ and $S_2$; in the third set of comparisons, $M_4$ will contain $S_1$, $S_2$, and $S_3$; and so on. Similarly, comparisons in table $M_j$ will be between $S_j$ and all successive subunits in $M_j$. Note that each successive table $M_{n+1}$ is smaller than its predecessors as subunits are eliminated in successive passes through step 130. After every subunit of table $M_n$ has been compared (140) the old table is replaced by the new table $M_{n+1}$, and the next round of comparisons are begun. The process stops (160) when a table $M_n$ is reached that contains no successive subunits to compare to the selected subunit $S_i$, i.e. $M_n=M_{n+1}$.

Preferably, minimally cross-hybridizing sets comprise subunits that make approximately equivalent contributions to duplex stability as every other subunit in the set. In this way, the stability of perfectly matched duplexes between every subunit and its complement is approximately equal. Guidance for selecting such sets is provided by published techniques for selecting optimal PCK primers and calculating duplex stabilities, e.g. Kychlik et al., Nucleic Acids Research, 17:8543–8551 (1989) and 18:6409–6412 (1990); Breslauer et al., Proc. Natl. Acad. Sci., 83:3746–3750 (1986); Wettour, Crit. Rev. Biochem. Mol. Biol., 26:227–259 (1991);and the like. For shorter tags, e.g. about 30 nucleotides or less, the algorithm described by Kychlik and Wettour is preferred, and for longer tags, e.g. about 30–35 nucleotides or greater, an algorithm disclosed by Suggs et al., pages 683–693 in Brown, editor, ICN-UCLA Syrup. Dev. Biol., Vol. 23 (Academic Press, New York, 1981) may be conveniently employed.

A preferred embodiment of minimally cross-hybridizing sets are those whose subunits are made up of three of the four natural nucleotides. As will be discussed more fully below, the absence of one type of nucleotide in the oligonucleotide tags permits target polynucleotides to be loaded onto solid phase supports by use of the 5'→3' exonuclease activity of a DNA polymerase. The following is an exemplary minimally cross-hybridizing set of subunits each comprising four nucleotides selected from the group consisting of A, G, and T:

TABLE I

| Word:     | $w_1$ | $w_2$ | $w_3$ | $w_4$ |
|-----------|-------|-------|-------|-------|
| Sequence: | GATT  | TGAT  | TAGA  | TTTG  |
| Word:     | $w_5$ | $w_6$ | $w_7$ | $w_8$ |
| Sequence: | GTAA  | AGTA  | ATGT  | AAAG  |

In this set, each member would form a duplex having three mismatched bases with the complement of every other member.

Further exemplary minimally cross-hybridizing sets are listed below in Table I. Clearly, additional sets can be generated by substituting different groups of nucleotides, or by using subsets of known minimally cross-hybridizing sets.

TABLE II

Exemplary Minimally Cross-Hybridizing Sets of 4-mer Subunits

| CATT | ACCC | AAAC | AAAG | AACA | AACG |
|------|------|------|------|------|------|
| CTAA | AGGG | ACCA | ACCA | ACAC | ACAA |
| TCAT | CACG | AGGG | AGGC | AGGG | AGGC |
| ACTA | CCGA | CACG | CACC | CAAG | CAAC |
| TACA | CGAC | CCGC | CCGG | CCGC | CCGG |
| TTTC | GAGC | CGAA | CGAA | CGCA | CGCA |
| ATCT | GCAG | GAGA | GAGA | GAGA | GAGA |
| AAAC | GGCA | GCAG | GCAC | GCCG | GCCC |
|      | AAAA | GGCC | GGCG | GGAC | GGAG |
| AAGA | AAGC | AAGG | ACAG | ACCG | ACGA |
| ACAC | ACAA | ACAA | AACA | AAAA | AAAC |
| AGCG | AGCG | AGCC | AGGC | AGGC | AGCG |
| CAAG | CAAG | CAAC | CAAC | CACC | CACA |
| CCCA | CCCC | CCCG | CCGA | CCGA | CCAG |
| CGGC | CGGA | CGGA | CGCG | CGAG | CGGC |
| GACC | GACA | GACA | GAGG | GAGG | GAGG |
| GCGG | GCGG | GCGC | GCCC | GCAC | GCCC |
| GGAA | GGAC | GGAG | GGAA | GGCA | GGAA |

The oligonucleotide tags of the invention and their complements are conveniently synthesized on an automated DNA synthesizer, e.g. an Applied Biosystems, Inc. (Foster City, California) model 392 or 394 DNA/RNA Synthesizer, using standard chemistries, such as phosphoramidite chemistry, e.g. disclosed in the following references: Beaucage and Iyer, Tetrahedron, 48:222–323 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are capable of specific hybridization. In some embodiments, tags may comprise naturally occuring nucleotides that permit processing or manipulation by enzymes, while the corresponding tag complements may comprise non-natural nucleotide analogs, such as peptide nucleic acids, or like compounds, that promote the formation of more stable duplexes during sorting.

When microparticles are used as supports, repertoires of oligonucleotide tags and tag complements are preferably generated by subunit-wise synthesis via "split and mix" techniques, e.g. as disclosed in Shortle et al., International patent application PCT/US93/03418. Briefly, the basic unit of the synthesis is a subunit of the oligonucleotide tag. Preferably, phosphoramidite chemistry is used and 3' phosphoramidite oligonucleotides are prepared for each subunit in a minimally cross-hybridizing set, e.g. for the set first listed above, there would be eight 4-mer 3'-phosphoramidites. Synthesis proceeds as disclosed by Shortle et al. or in direct analogy with the techniques employed to generate diverse oligonucleotide libraries using nucleosidic monomers, e.g. as disclosed in Tetenius et al., Genomics, 13:718–725 (1992); Welsh et al., Nucleic Acids Research, 19:5275–5279 (1991); Grothues et al., Nucleic Acids Research, 21:1321–1322 (1993); Hartley, European patent application 90304496.4; Lain et al., Nature, 354:82–84 (1991); Zuckerman et al., Int. I. Pept. Protein Research, 40:498–507 (1992); and the like. Generally, these techniques simply call for the application of mixtures of the activated toohomers to the growing oligonucleotide during the coupling steps.

Double stranded forms of tags are made by separately synthesizing the complementary strands followed by mixing under conditions that permit duplex formation. Such duplex tags may then be inserted into cloning vectors along with target polynucleotides for sorting and manipulation of the target polynucleotide in accordance with the invention.

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al., Proc. Natl. Acad. Sci., 88:9397–9401 (1991); Roberts et al., Science, 258:1463–1466 (1992); Distefano et al., Proc. Natl. Acad. Sci., 90:1179–1183 (1993); Mergny et al., Biochemistry, 30:9791–9798 (1991); Cheng et al., J. Am. Chem. Soc., 114:4465–4474 (1992); Beat and Dervan, Nucleic Acids Research, 20:2773–2776 (1992); Beat and Dervan, I. Am. Chem. Soc., 114:4976–982 (1992); Giovannangeli et al., Proc. Natl. Acad. Sci., 89:8631–8635 (1992); Moser and Dervan, Science, 238:645–650 (1987); McShan et al., J. Biol. Chem., 267:5712–5721 (1992); Yoon et al., Proc. Natl. Acad. Sci., 89:3840–3844 (1992); Blume et al., Nucleic Acids Research, 20:1777–1784 (1992); Thuong and Helene, Angew. Chem. Int. Ed. Engl. 32:666–690 (1993); and the like. Conditions for annealing single-stranded or duplex tags to their single-stranded or duplex complements are well known, e.g. Ji et al., Anal. Chem. 65:1323–1328 (1993).

Oligonucleotide tags of the invention may range in length from 12 to 60 nucleotides or basepairs. Preferably, oligonucleotide tags range in length from 18 to 40 nucleotides or basepairs. More preferably, oligonucleotide tags range in length from 25 to 40 nucleotides or basepairs. Most preferably, oligonucleotide tags are single stranded and specific hybridization occurs via Watson-Crick pairing with a tag complement.

Attaching Tags to Molecules

Oligonucleotide tags may be attached to many different classes of molecules by a variety of reactive functionalities well known in the art, e.g. Haugland, Handbook of Fluorescent Probes and Research Chemicals (Molecular Probes, Inc., Eugene, 1992); Khanna et al., U.S. Pat. No. 4,318,846; or the like. Table III provides exemplary functionalities and counterpart reactive groups that may reside on oligonucleotide tags or the molecules of interest. When the functionalities and counterpart reactants are reacted together, after activation in some cases, a linking group is formed. Moreover, as described more fully below, tags may be synthesized simultaneously with the molecules undergoing selection to form combinatorial chemical libraries.

encoded within a polynucleotide attached to the tag, as taught by Brenner and Lerner (cited above). However, after a selection event, instead of amplifying then sequencing the tag of the selected molecule, the tag itself or an additional coding segment can be sequenced directly-using a so-called "single base" approach described below-after releasing the molecule of interest, e.g. by restriction digestion of a site engineered into the tag. Clearly, any molecule produced by a sequence of chemical reaction steps compatible with the simultaneous synthesis of the tag moieties can be used in the generation of combinatorial libraries.

Conveniently there is a wide diversity of phosphate-linked monomers available for generating combinatorial libraries. The following references disclose several phosphoramidite and/or hydrogen phosphonate monomers suitable for use in the present invention and provide guidance for their synthesis and inclusion into oligonucleotides: Newton et al., Nucleic Acids Research, 21:1155–1162 (1993); Griffin et al., J. Am. Chem. Soc., 114:7976–7982 (1992); Jaschke et al., Tetrahedron Letters, 34:301–304 (1992); Ma et al., International application PCT/CA92/00423; Zon et al., International application PCT/US90/06630; Durand et al., Nucleic Acids Research, 18:6353–6359 (1990); Salunkhe et al., J. Am. Chem. Soc., 114:8768–8772 (1992); Urdea et al., U.S. Pat. No. 5,093,232; Ruth, U.S. Pat. No. 4,948,882; Cruickshank, U.S. Pat. No. 5,091,519; Haralambidis et al., Nucleic Acids Research, 15:4857–4876 (1987); and the like.

TABLE III

Reactive Functionalities and Their Counterpart Reactants and Resulting Linking Groups

| Reactive Functionality | Counterpart Functionality | Linking Group |
|---|---|---|
| —NH$_2$ | —COOH | —CO—NH— |
| —NH$_2$ | —NCO | —NHCONH— |
| —NH$_2$ | —NCS | —NHCSNH— |
| —NH$_2$ | 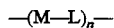 triazine-Cl | triazine-NH— |
| —SH | —C=C—CO— | —S—C—C—CO— |
| —NH$_2$ | —CHO | —CH$_2$NH— |
| —NH$_2$ | —SO$_2$Cl | —SO$_2$NH— |
| —OH | —OP(NCH(CH$_3$)$_2$)$_2$ | —OP(=O)(O)O— |
| —OP(=O)(O)S | —NHC(=O)CH$_2$Br | —NHC(—=O)CH$_2$SP(=O)(O)O— |

A class of molecules particularly convenient for the generation of combinatorial chemical libraries includes linear polymeric molecules of the form:

—(M—L)$_n$— wherein L is a linker moiety and M is a monomer that may selected from a wide range of chemical structures to provide a range of functions from serving as an inert non-sterically hindering spacer moiety to providing a reactive functionality which can serve as a branching point to attach other components, a site for attaching labels; a site for attaching oligonucleotides or other binding polymers for hybridizing or binding to a therapeutic target; or as a site for attaching other groups for affecting solubility, promotion of duplex and/or triplex formation, such as intercalators, alkylating agents, and the like. The sequence, and therefore composition, of such linear polymeric molecules may be More particularly, M may be a straight chain, cyclic, or branched organic molecular structure containing from 1 to 20 carbon atoms and from 0 to 10 heteroatoms selected from the group consisting of oxygen, nitrogen, and sulfur. Preferably, M is alkyl, alkoxy, alkenyl, or aryl containing from 1 to 16 carbon atoms; a heterocycle having from 3 to 8 carbon atoms and from 1 to 3 heteroatoms selected from the group consisting of oxygen, nitrogen, and sulfur; glycosyl; or nucleosidyl. More preferably, M is alkyl, alkoxy, alkenyl, or aryl containing from 1 to 8 carbon atoms; glycosyl; or nucleosidyl.

Preferably, L is a phosphorus(V) linking group which may be phosphodiester, phosphotriester, methyl or ethyl phosphonate, phosphorothioate, phosphorodithioate, phosphoramidate, or the like. Generally, linkages derived from phosphoramidite or hydrogen phosphonate precursors are preferred so that the linear polymeric units of the invention can be conveniently synthesized with commercial automated DNA synthesizers, e.g. Applied Biosystems, Inc. (Foster City, CA) model 394, or the like.

n may vary significantly depending on the nature of M and L. Usually, n varies from about 3 to about 100. When M is a nucleoside or analog thereof or a nucleoside-sized monomer and L is a phosphorus(V) linkage, then n varies from about 12 to about 100. Preferably, when M is a nucleoside or analog thereof or a nucleoside-sized monomer and L is a phosphorus(V) linkage, then n varies from about 12 to about 40.

Peptides are another preferred class of molecules to which tags of the invention are attached. Synthesis of peptide-oligonucleotide conjugates which may be used in the invention is taught in Nielsen et al, J. Am. Chem. Soc., 115:9812–9813 (1993); Haralambidis et al. (cited above) and International patent application PCT/AU88/004417; Truffert et al., Tetrahedron Letters, 35:2353–2356 (1994); de la Torre et al., Tetrahedron Letters, 35:2733–2736 (1994); and like references. Preferably, peptide-oligonucleotide conjugates are synthesized as described below. Peptides synthesized in accordance with the invention may consist of the natural amino acid monomers or non-natural monomers, including the D isomers of the natural amino acids and the like.

Combinatorial Chemical Libraries

Combinatorial chemical libraries employing tags of the invention are preferably prepared by the method disclosed in Nielsen et al. (cited above) and illustrated in FIG. 4 for a particular embodiment. Briefly, a solid phase support, such as CPG, is derivatized with a cleavable linker that is compatible with both the chemistry employed to synthesize the tags and the chemistry employed to synthesize the molecule that will undergo some selection process. Preferably, tags are synthesized using phosphoramidite Chemistry as described above and with the modifications recommended by Nielsen et al. (cited above); that is, DMT-5'-O-protected 3'-phosphoramidite-derivatized subunits having methyl-protected phosphite and phosphate moieties are added in each synthesis cycle. Library compounds are preferably monomers having Fmoc-or equivalent--protecting groups masking the functionality to which successive toohomer will be coupled. A suitable linker for chemistries employing both DMT and Fmoc protecting groups (referred to herein as a safcosine linker) is disclosed by Brown et al., J. Chem. Soc. Chem. Commun., 1989:891–893, which reference is incorporated by reference.

Figure 4:
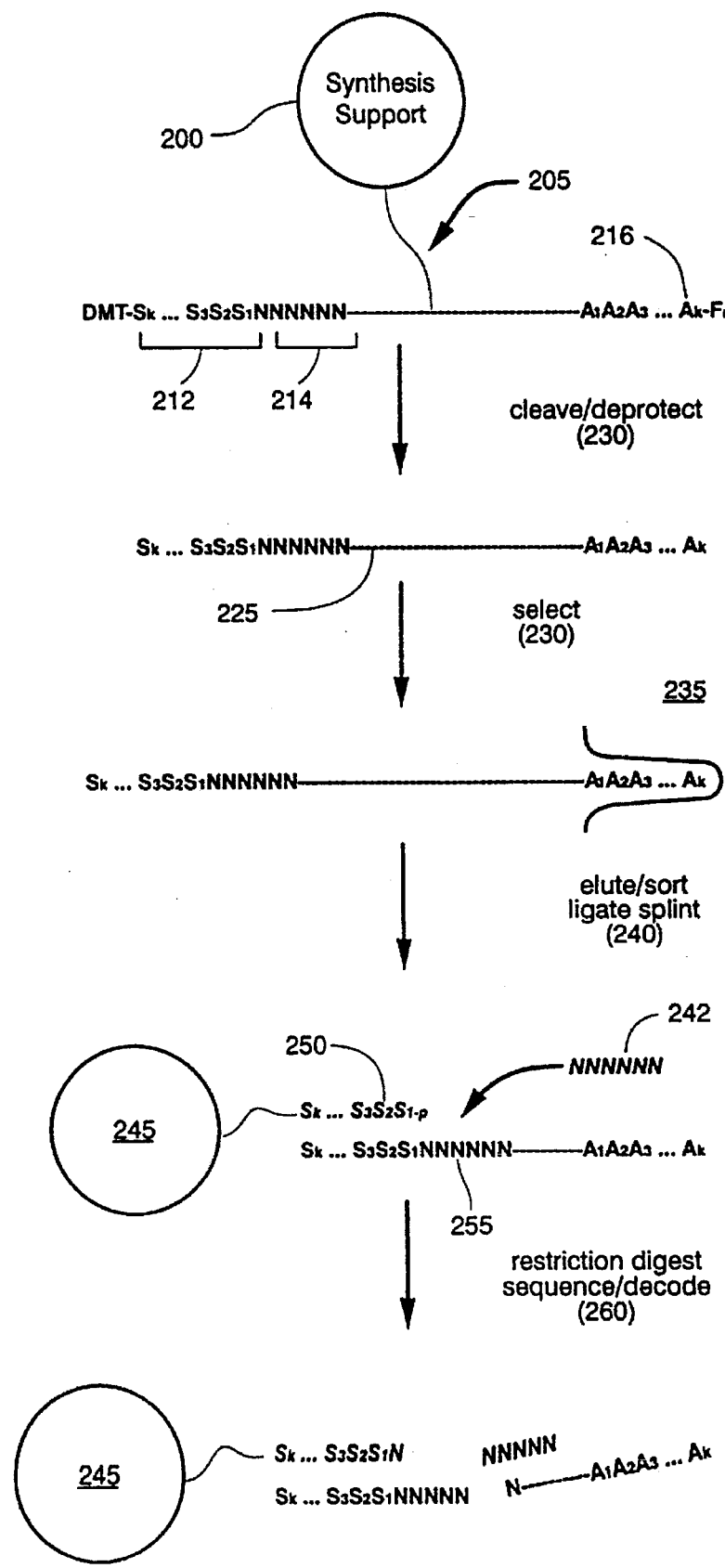
FIG. 4 illustrates a scheme for synthesizing and using a combinatorial chemical library in which member compounds are labeled with oligonucleotide tags in accordance with the invention.

FIG. 4 illustrates a scheme for generating a combinatorial chemical library of peptides conjugated to oligonucleotide tags. Solid phase support 200 is derivatized by sarcosine linker 205 (exemplified in the formula below) as aught by Nielsen et al. (cited above), which has an extended linking moiety to facilitate reagent access.

(CPG)—NHC(O)CN(CH$_3$)C(O)CH$_2$CH$_2$C(O)O(CH$_2$)$_6$NHC(O)CH$_2$(O—DMT)NC(O)—CH$_2$O CH$_2$CHO)$_2$CH$_2$CH$_2$NHC(O)CH$_2$O(CH$_2$CH$_2$O)$_2$CH$_2$CH$_2$NH—Fmoc Here "CPG" represents a controlled-pore glass support, "DMT" represents dimethoxytrityl, and "Fmoc" represents 9-fluorenylmethoxycarbonyl. In a preferred embodiment, an oligonucleotide segment 214 is synthesized initially so that in double stranded form a restriction endonuclease site is provided for cleaving the library compound after sorting onto a microparticle, or like substrate. Synthesis proceeds by successive alternative additions of subunits S$_1$, S$_2$, S$_3$, and the like, to form tag 212, and their corresponding library compound monomers A$_1$, A$_2$, A$_3$, and the like, to form library compound 216. A "split and mix" technique is employed to generate diversity.

The subunits in a minimally cross-hybridizing set code for the toohomer added in the library compound. Thus, a nine word set can unambiguously encode library compounds constructed from nine toohomers. If some ambiguity is acceptable, then a single subunit may encode more than one toohomer.

After synthesis is completed, the product is cleaved and deprotected (220) to form tagged library compound 225, which then undergoes selection 230, e.g. binding to a predetermined target 235, such as a protein. The subset of library compounds recovered from selection process 230 is then sorted (240) onto a solid phase support 245 via their tag moieties (there complementary subunits and nucleotides are shown in italics). After ligating oligonucleotide splint 242 to tag. complement 250 to form restriction site 255, the conjugate is digested with the corresponding restriction endonuclease to cleave the library compound, a peptide in the example of FIG. 4, from the oligonucleotide moiety. The sequence of the tag, and hence the identity of the library compound, is then determined by the preferred single base sequencing technique of the invention, described below.

Solid Phase Supports

Solid phase supports for use with the invention may have a wide variety of forms, including microparticles, beads, and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Preferably, either a population of discrete particles are employed such that each has a uniform coating, or population, of complementary sequences of the same tag (and no other), or a single or a few supports are employed with spacially discrete regions each containing a uniform coating, or population, of complementary sequences to the same tag (and no other). In the latter embodiment, the area of the regions may vary according to particular applications; usually, the regions range in area from several μm$^2$, e.g. 3–5, to several hundred μm$^2$, e.g. 100–500. Preferably, such regions are spacially discrete so that signals generated by events, e.g. fluorescent emissions, at adjacent regions can be resolved by the detection system being employed. In some applications, it may be desirable to have regions with uniform coatings of more than one tag complement, e.g. for simultaneous sequence analysis, or for bringing separately tagged molecules into close proximity.

Tag complements may be used with the solid phase support that they are synthesized on, or they may be separately synthesized and attached to a solid phase support for use, e.g. as disclosed by Lund et al., Nucleic Acids Research, 16:10861–10880 (1988); Albretsen et al., Anal. Biochem., 189:40–50 (1990); Wolfet at, Nucleic Acids Research, 15:2911–2926 (1987); or Ghosh et al., Nucleic Acids Research, 15:5353–5372 (1987). Preferably, tag complements are synthesized on and used with the same solid phase support, which may comprise a variety of forms and include a variety of linking moieties. Such supports may comprise microparticles or arrays, or matrices, of regions where uniform populations of tag complements are synthesized. A wide variety of microparticle supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section & pages 11–147, vol. 44 (Academic Press, New York, 1976); U.S. Pat. Nos. 4,678, 814; 4,413,070; and 4,046,720; and Port, Chapter 19, in Agrawal, editor, Methods in Molecular Biology, Vol. 20, (Humana Press, Totowa, NJ, 1993). Microparticle supports further include commercially available nucleoside-derivatized CPG and polystyrene beads (e.g. available from Applied Biosystems, Foster City, CA); derivatized magnetic beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on the conditions under which the tags are used. For example, in applications involving successive processing with enzymes, supports and linkers that minimize steric hinderance of the enzymes and that facilitate access to substrate are preferred. Exemplary linking moieties are disclosed in Pon et al., Biotechniques, 6:768–775 (1988); Webb, U.S. Pat. No. 4,659,774; Barany et al., International patent application PCT/US91/06103; Brown et al., J. Chem. Soc. Commun., 1989: 891–893; Damha et al., Nucleic Acids Research, 18:3813–3821 (1990); Beattie et al., Clinical Chemistry, 39:719–722 (1993); Maskos and Southern, Nucleic Acids Research, 20:1679–1684 (1992); and the like.

As mentioned above, tag complements may also be synthesized on a single (or a few) solid phase support to form an array of regions uniformly coated with tag complements. That is, within each region in such an array the same tag complement is synthesized. Techniques for synthesizing such arrays are disclosed in McCall et al., International application PCT/US93/03767; Pease et al., Proc. Natl. Acad. Sci., 91:5022–5026 (1994); Southern and Maskos, International application PCT/GB89/01114; Maskos and Southern (cited above); Southern et al., Genomics, 13:1008–1017 (1992); and Maskos and Southern, Nucleic Acids Research, 21:4663–4669 (1993).

Preferably, the invention is implemented with microparticles or beads uniformly coated with complements of the same tag sequence. Microparticle supports and methods of covalently or noncovalently linking oligonucleotides to their surfaces are well known, as exemplified by the following references: Beaucage and Iyer (cited above); Gait, editor, Oligonucleotide Synthesis: A Practical Approach (IRL Press, Oxford, 1984); and the references cited above. Generally, the size and shape of a microparticle is not critical; however, microparticles in the size range of a few, e.g. 1–2, to several hundred, e.g. 200–1000 μm diameter are preferable, as they facilitate the construction and manipulation of large repertoires of oligonucleotide tags with minimal reagent and sample usage.

Preferably, commercially available controlled-pore glass (CPG) or polystyrene supports are employed as solid phase supports in the invention. Such supports come available with base-labile linkers and initial nucleosides attached, e.g. Applied Biosystems (Froster City, CA). Preferably, microparticles having pore size between 500 and 1000 angstroms are employed.

Attaching Target Polynucleotides to Microparticles

An important aspect of the invention is the sorting of populations of identical polynucleotides, e.g. from a cDNA library, and their attachment to microparticles or separate regions of a solid phase support such that each microparticle or region has only a single kind of polynucleotide. This latter condition can be essentially met by ligating a repertoire of tags to a population of polynucleotides followed by cloning and sampling of the ligated sequences. A repertoire of oligonucleotide tags can be ligated to a population of polynucleotides in a number of ways, such as through direct enzymatic ligation, amplification, e.g. via PCR, using primers containing the tag sequences, and the like. The initial ligating step produces a very large population of tag-polynucleotide conjugates such that a single tag is generally attached to many different polynucleotides. However, by taking a sufficiently small sample of the conjugates, the probability of obtaining "doubles," i.e. the same tag on two different polynucleotides, can be made negligible. (Note that it is also possible to obtain different tags with the same polynucleotide in a sample. This case is simply leads to a polynucleotide being processed, e.g. sequenced, twice). As explain more fully below, the probability of obtaining a double in a sample can be estimated by a Poisson distribution since the number of conjugates in a sample will be large, e.g. on the order of thousands or more, and the probability of selecting a particular tag will be small because the tag repertoire is large, e.g. on the order of tens of thousand or more. Generally, the larger the sample the greater the probability of obtaining a double. Thus, a design trade-off exists between selecting a large sample of tag-polynucleotide conjugates-which for example, ensures adequate coverage of a target polynucleotide in a shotgun sequencing operation, and selecting a small sample which ensures that a minimal number of doubles will be present. In most embodiments, the presence of doubles merely adds an additional source of noise or, in the case of sequencing, a minor complication in scanning and signal processing, as microparticles giving multiple fluorescent signals can simply be ignored. As used herein, the term "substantially all" in reference to attaching tags to molecules, especially polynucleotides, is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing, substantially all means that at least eighty percent of the tags have unique polynucleotides attached. More preferably, it means that at least ninety percent of the tags have unique polynucleotides attached. Still more preferably, it means that at least ninety-five percent of the tags have unique polynucleotides attached. And, most preferably, it means that at least ninety-nine percent of the tags have unique polynucleotides attached.

Preferably, when the population of polynucleotides is messenger RNA ((mRNA), oligonucleotides tags are attached by reverse transcribing the mRNA with a set of primers containing complements of tag sequences. An exemplary set of such primers could have the following sequence (SEQ ID NO: 5):

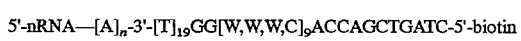

5'-mRNA—[A]$_n$-3'-[T]$_{19}$GG[W,W,W,C]$_9$ACCAGCTGATC-5'-biotin where "[W,W,W,C]$_9$" represents the sequence of an oligonucleotide tag of nine subunits of four nucleotides each and "[W,W,W,C]" represents the subit sequences listed above, i.e. "W" represents T or A. The underlined sequences identify an optional restriction endonuclease site that can be used to release the polynucleotide from attachment to a solid phase support via the biotin, if one is employed. For the above primer, the complement attached to a microparticle could have the form:

5'-[G,W,W,W]₉TGG-linker-microparticle

After reverse transcription, the (mRNA is removed, e.g. by RNase H digestion, and the second strand of the cDNA is synthesized using, for example, a primer of the following form (SEQ ID NO: 6):

5'-NRRGATCYNNN-3' where N is any one of& T, G, or C; R is a purine-containing nucleotide, and Y is a pyrimidine-containing nucleotide. This particular primer creates a Bst Yl restriction site in the resulting double stranded DNA which, together with the Sal I site, facilitates cloning into a vector with, for example, Bam HI and Xho I sites. After Bst Yl and Sal I digestion, the exemplary conjugate would have the form:

5'-RCGACCA[C,W,W,W]₉GG[T]₁₉- cDNA -NNNR

GGT[G,W,W,W]₉CC[A]₁₉- rDNA -NNNYCTAG-5'

Preferably, when the ligase-based method of sequencing is employed, the Bst Yl and Sal I digested fragments are cloned into a Bam HI-/Xho I-digested vector having the following single-copy restriction sites (SEQ ID NO:1):

5'-GAGGATGCCTTTATGGATCCACTCGAGATCCCAATCCA-3'
     FokI         BamHI    XhoI

This adds the Fok I site which will allow initiation of the sequencing process discussed more fully below.

A general method for exposing the single stranded tag after amplification involves digesting a target polynucleotide-containing conjugate with the 5'→3' exocunlease activity of T4 DNA polymerase, or a like enzyme. When used in the presence of a single nucleoside triphosphate, such a polymerase will cleave nucleotides from 3' recessed ends present on the non-template strand of a double stranded fragment until a complement of the single nucleoside triphosphate is reached on the template strand. When such a nucleotide is reached the digestion effectively ceases, as the polymerase's extension activity adds nucleotides at a higher rate than the excision activity removes nucleotides. Consequently, tags constructed with three nucleotides are readily prepared for loading onto solid phase supports.

The technique may also be used to preferentially methylate interior Fok I sites of a target polynucleotide while leaving a single Fok I site at the terminus of the polynucleotide unmethylated. First, the terminal Fok I site is rendered single stranded using a polymerase with deoxycytidine triphosphate. The double standard portion of the fragment is then methylated, after which the single stranded terminus is filled in with a DNA polymerase in the presence of all four nucleoside triphosphates, thereby regenerating the Fok I site.

After the oligonucleotide tags are prepared for specific hybridization, e.g. by rendering them single stranded as described above, the polynucleotides are mixed with microparticles containing the complementary sequences of the tags under conditions that favor the formation of perfectly matched duplexes between the tags and their complements. There is extensive guidance in the literature for creating these conditions. Exemplary references providing such guidance include Wetmur, Critical Reviews in Biochemistry and Molecular Biology, 26:227–259 (1991); Sambrook et al., Molecular Cloning: A Laboratory Manual, 2nd Edition (Cold Spring Harbor Laboratory, New York, 1989); and the like. Preferably, the hybridization conditions are sufficiently stringent so that only perfectly matched sequences form stable duplexes. Under such conditions the polynucleotides specifically hybridized through their tags are ligated to the complementary sequences attached to the microparticles. Finally, the microparticles are washed to remove unligated polynucleotides.

When CPG microparticles conventionally employed as synthesis supports are used, the density of tag complements on the microparticle surface is typically greater than that necessary for some sequencing operations. That is, in sequencing approaches that require successive treatment of the attached polynucleotides with a variety of enzymes, densely spaced polynucleotides may tend to inhibit access of the relatively bulky enzymes to the polynucleotides. In such cases, the polynucleotides are preferably mixed with the microparticles so that tag complements are present in significant excess, e.g. from 10:1 to 100:1, or greater, over the polynucleotides. This ensures that the density of polynucleotides on the microparticle surface will not be so high as to inhibit enzyme access. Preferably, the average inter-polynucleotide spacing on the microparticle surface is on the order of 30–100 nm. Guidance in selecting ratios for standard CPG supports and Ballotini beads (a type of solid glass support) is found in Maskos and Southern, Nucleic Acids Research, 20:1679–1684 (1992). Preferably, for sequencing applications, standard CPG beads of diameter in the range of 20–50 μm are loaded with about $10^5$ polynucleotides.

The above method may be used to fingerprint mRNA populations when coupled with the parallel sequencing methodology described below. Partial sequence information is obtained simultaneously from a large sample, e.g. ten to a hundred thousand, of cDNAs attached to separate microparticles as described in the above method. The frequency distribution of partial sequences can identify mRNA populations from different cell or tissue types, as well as from diseased tissues, such as cancers. Such mRNA fingerprints are useful in monitoring and diagnosing disease states.

Single Base DNA Sequencing

The present invention can be employed with conventional methods of DNA sequencing, e.g. as disclosed by Hultman et al., Nucleic Acids Kesearch, 17:4937–4946 (1989). However, for parallel, or simultaneous, sequencing of multiple polynucleotides, a DNA sequencing methodology is preferred that requires neither electrophoretic separation of closely sized DNA fragments nor analysis of cleaved nucleotides by a separate analytical procedure, as in peptide sequencing. Preferably, the methodology permits the stepwise identification of nucleotides, usually one at a time, in a sequence through successive cycles of treatment and detection. Such methodologies are referred to herein as "single base" sequencing methods. Single base approaches are disclosed in the following references: Cheeseman, U.S. Pat. No. 5,302,509; Tsien et al., International application WO 91/06678; Rosenthal et al., International application WO 93/21340; Canard et al., Gene, 148:1–6 (1994); and Metzker et al., Nucleic Acids Kesearch, 22:4259–4267 (1994).

A "single base" method of DNA sequencing which is suitable for use with the present invention and which requires no electrophoretic separation of DNA fragments is described in co-pending U.S. patent application Ser. No. 08/280,441 filed 25 Jul. 1994, which application is incorporated by reference. The method comprises the following steps: (a) ligating a probe to an end of the polynucleotide having a protruding strand to form a ligated complex, the probe having a complementary protruding strand to that of the polynucleotide and the probe having a nuclease recognition site; (b) removing unligated probe from the ligated complex; (c) identifying one or more nucleotides in the protruding strand of the polynucleotide by the identity of the ligated probe; (d) cleaving the ligated complex with a nuclease; and (e) repeating steps (a) through (d) until the nucleotide sequence of the polynucleotide is determined. As is described more fully below, identifying the one or more nucleotides can be carried out either before or after cleavage of the ligated complex from the target polynucleotide. Preferably, whenever natural protein endonucleases are employed, the method further includes a step of methylating the target polynucleotide at the start of a sequencing operation.

An important feature of the method is the probe ligated to the target polynucleotide. A preferred form of the probes is illustrated in FIG. 1a. Generally, the probes are double stranded DNA with a protruding strand at one end 10. The probes contain at least one nuclease recognition site 12 and a spacer region 14 between the recognition site and the protruding end 10. Preferably, probes also include a label 16, which in this particular embodiment is illustrated at the end opposite of the protruding strand. The probes may be labeled by a variety of means and at a variety of locations, the only restriction being that the labeling means selected does not inteffer with the ligation step or with the recognition of the probe by the nuclease.

It is not critical whether protruding strand 10 of the probe is a 5' and 3' end. However, it is important that the protruding strands of the target polynucleotide and probes be capable of forming perfectly matched duplexes to allow for specific ligation. If the protruding strands of the target polynucleotide and probe are different lengths the resulting gap can be filled in by a polymerase prior to ligation, e.g. as in "gap LCR" disclosed in Backman et al., European patent application 91100959.5. Preferably, the number of nucleotides in the respective protruding strands are the same so that both strands of the probe and target polynucleotide are capable of being ligated without a filling step. Preferably, the protruding strand of the probe is from 2 to 6 nucleotides long. As indicated below, the greater the length of the protruding strand, the greater the complexity of the probe mixture that is applied to the target polynucleotide during each ligation and cleavage cycle.

The complementary strands of the probes are conveniently synthesized on an automated DNA synthesizer, e.g. an Applied Biosystems, Inc. (Foster City, Calif.) model 392 or 394 DNA/RNA Synthesizer, using standard chemistries. After synthesis, the complementary strands are combined to form a double stranded probe. Generally, the protruding strand of a probe is synthesized as a mixture, so that every possible sequence is represented in the protruding portion. For example, if the protruding portion consisted of four nucleotides, in one embodiment four mixtures are prepared as follows:

$X_1X_2 \ldots X_i$NNNA, $X_1X_2 \ldots X_i$NNNC, $X_1X_2 \ldots X_i$NNNG, nd $X_1X_2 \ldots X_i$NNNT where the "NNNs" represent every possible 3-mer and the "Xs" represent the duplex forming portion of the strand. Thus, each of the four probes listed above contains $4^3$ or 64 distinct sequences; or, in other words, each of the four probes has a degeneracy of 64. For example, $X_1, X_2 \ldots X_i$NNNA contains the following sequences:

$X_1X_2 \ldots X_i$AAAA $X_1X_2 \ldots X_i$AACA $X_1X_2 \ldots X_i$AAGA $X_1X_2 \ldots X_i$AATA $X_1X_2 \ldots X_i$ACAA $X_1X_2 \ldots X_i$TGTA $X_1X_2 \ldots X_i$TTAA $X_1X_2 \ldots X_i$TTCA $X_1X_2 \ldots X_i$TTGA $X_1X_2 \ldots X_i$ TTTA Such mixtures are readily synthesized using well known techniques, e.g. as disclosed in Telenius et al. (cited above). Generally, these techniques simply call for the application of mixtures of the activated monomers to the growing oligonucleotide during the coupling steps where one desires to introduce the degeneracy. In some embodiments it may be desirable to reduce the degeneracy of the probes. This can be accomplished using degeneracy reducing analogs, such as deoxyinosine, 2-aminopurine, or the like, e.g. as taught in Kong Thoo Lin et al., Nucleic Acids Research,. 20:5149–5152, or by U.S. Pat. No. 5,002,867.

Preferably, for oligonucleotides with phosphodiester linkages, the duplex forming region of a probe is between about 12 to about 30 basepairs in length; more preferably, its length is between about 15 to about 25 basepairs.

When conventional ligases are employed in the invention, as described more fully below, the 5' end of the probe may be phosphorylated in some embodiments. A 5' monophosphate can be attached to a second oligonucleotide either chemically or enzymatically with a kinase, e.g. Sambrook et al. (cited above). Chemical phosphorylation is described by Horn and Urdea, Tetrahedron Lett., 27:4705 (1986), and reagents for carrying out the disclosed protocols are commercially available, e.g. 5' Phosphate-ON™ from Clontech Laboratories (Palo Alto, Calif.). Thus, in some embodiments, probes may have the form:

$5'-X_1X_2 \ldots X_i$TTGA $Y_1Y_2 \ldots Y_{ip}$ where the Y's are the complementary nucleotides of the X's and "p" is a monophosphate group.

The above probes can be labeled in a variety of ways, including the direct or indirect attachment of radioactive moieties, fluorescent moieties, colorimetric moieties, chemiluminescent markers, and the like. Many comprehensive reviews of methodologies for labeling DNA and constructing DNA probes provide guidance applicable to constructing probes of the present invention. Such reviews include Kricka, editor, Nonisotopic DNA Probe Techniques (Academic Press, San Diego, 1992); Haugiand, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Kessler, editor, Nonradioactive Labeling and Detection of Biomolecules (Springer-Verlag, Berlin, 1992); Wetmur (cited above); and the like.

Preferably, the probes are labeled with one or more fluorescent dyes, e.g. as disclosed by Menchen et al., U.S. Pat. No. 5,188,934; Begot et al. International application PCT/US90/05565.

In accordance with the method, a probe is ligated to an end of a target polynucleotide to form a ligated complex in each cycle of ligation and cleavage. The ligated complex is the double stranded structure formed after the protruding.

strands of the target polynucleotide and probe anneal and at least one pair of the identically oriented strands of the probe and target are ligated, i.e. are caused to be covalently linked to one another. Ligation can be accomplished either enzymatically or chemically. Chemical ligation methods are well known in the art, e.g. Ferris et al., Nucleosides & Nucleotides, 8:407–414 (1989); Shabarova et al., Nucleic Acids Research, 19:4247–4251 (1991); and the like. Preferably, however, ligation is carried out enzymatically using a ligase in a standard protocol. Many ligases are known and are suitable for use in the invention, e.g. Lehman, Science, 186:790–797 (1974); Engler et al., DNA Ligases, pages 3–30 in Boyer, editor, The Enzymes, Vol. 15B (Academic Press, New York, 1982); and the like. Preferred ligases include T4 DNA ligase, T7 DNA ligase, E. coli DNA ligase, Taq ligase, Pfu ligase, and Tth ligase. Protocols for their use are well known, e.g. Sambrook et al. (cited above); Barany, PCR Methods and Applications, 1:5–16 1991); Marsh et at., Strategies, 5:73–76 (1992); and the like. Generally, ligases require that a 5' phosphate group be present for ligation to the 3' hydroxyl of an abutting strand. This is conveniently provided for at least one strand of the target polynucleotide by selecting a nuclease which leaves a 5' phosphate, e.g. as Fok I.

In an embodiment of the sequencing method employing unphosphorylated probes, the step of ligating includes (i) ligating the probe to the target polynucleotide with a ligase so that a ligated complex is formed having a nick on one strand, (ii) phosphorylating the 5' hydroxyl at the nick with a kinase using conventional protocols, e.g. Sambrook et al. (cited above), and (ii) ligating again to covalently join the strands at the nick, i.e. to remove the nick.

Apparatus for Observing Enzymatic Processes and/ or Binding Events at Microparticle Surfaces An objective of the invention is to sort identical molecules, particularly polynucleotides, onto the surfaces of microparticles by the specific hybridization of tags and their complements. Once such sorting has taken place, the presence of the molecules or operations performed on them can be detected in a number of ways depending on the nature of the tagged molecule, whether microparticles are detected separately or in "batches," whether repeated measurements are desked, and the like. Typically, the sorted molecules are exposed to ligands for binding, e.g. in drug development, or are subjected chemical or enzymatic processes, e.g. in polynucleotide sequencing. In both of these uses it is often desirable to simultaneously observe signals corresponding to such events or processes on large numbers of microparticles. Microparticles carrying sorted molecules (referred to herein as "loaded" microparticles) lend themselves to such large scale parallel operations, e.g. as demonstrated by Lain et al. (cited above).

Preferably, whenever light-generating signals, e.g. chemiluminescent, fluorescent, or the like, are employed to detect events or processes, loaded microparticles are spread on a planar substrate, e.g. a glass slide, for examination with a scanning system, such as described in International patent applications PCT/US91/09217 and PCT/NL90/00081. The scanning system should be able to reproducibly scan the substrate and to define the positions of each microparticle in a predetermined region by way of a coordinate system. In polynucleotide sequencing applications, it is important that the positional identification of microparticles be repeatable in successive scan steps.

Such scanning systems may be constructed from commercially available components, e.g. x—y translation table controlled by a digital computer used with a detection system comprising one or more photomultiplier tubes, or alternatively, a CCD array, and appropriate optics, e.g. for exciting, collecting, and sorting fluorescent signals. In some embodiments a confocal optical system may be desirable. An exemplary scanning system suitable for use in four-color sequencing is illustrated diagrammatically in FIG. 5. Substrate 300, e.g. a microscope slide with fixed microparticles, is placed on x—y translation table 302, which is connected to and controlled by an appropriately programmed digital computer 304 which may be any of a variety of commercially available personal computers, e.g. 486-based machines or PowerPC model 7100 or 8100 available form Apple Computer (Cupertino, CA). Computer software for table translation and data collection functions can be provided by commercially available laboratory software, such as Lab Windows, available from National Instruments.

Figure 5:
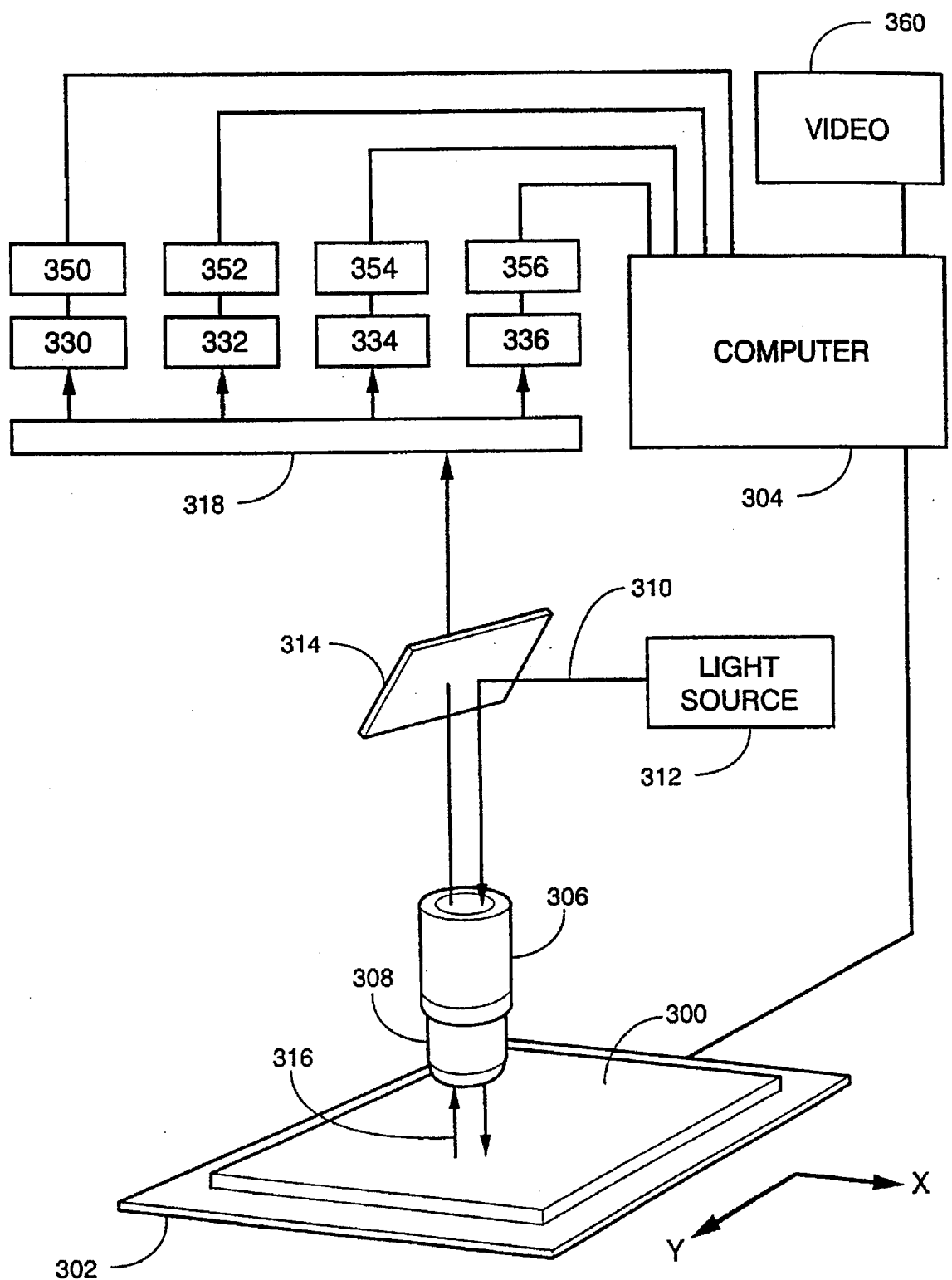
FIG. 5 diagrammatically illustrates an apparatus for carrying out parallel operations, such as polynucleotide sequencing, in accordance with the invention.

Substrate 300 and table 302 are operationally associated with microscope 306 having one or more objective lenses 308 which are capable of collecting and delivering light to microparticles fixed to substrate 300. Excitation beam 310 from light source 312, which is preferably a laser, is directed to beam splitter 314, e.g. a dichroic mirror, which re-directs the beam through microscope 306 and objective lens 308 which, in turn, focuses the beam onto substrate 300. Lens 308 collects fluorescence 316 emitted from the microparticles and directs it through beam splitter 314 to signal distribution optics 318 which, in turn, directs fluorescence to one or more suitable opto-electronic devices for converting some fluorescence characteristic, e.g. intensity, lifetime, or the like, to an electrical signal. Signal distribution optics 318 may comprise a variety of components standard in the art, such as bandpass filters, fiber optics, rotating mirrors, fixed position mirrors and lenses, diffraction gratings, and the like. As illustrated in FIG. 5, signal distribution optics 318 directs fluorescence 316 to four separate photomultiplier tubes, 330, 332, 334, and 336, whose output is then directed to pre-amps and photon counters 350, 352, 354, and 356. The output of the photon counters is collected by computer 304, where it can be stored, analyzed, and viewed on video 360. Alternatively, signal distribution optics 318 could be a diffraction grating which directs fluorescent signal 318 onto a CCD array.

The stability and reproducibility of the positional localization in scanning will determine, to a large extent, the resolution for separating closely spaced microparticles. Preferably, the scanning systems should be capable of resolving closely spaced microparticles, e.g. separated by a particle diameter. Thus, for most applications, e.g. using CPG microparticles, the scanning system should at least have the capability of resolving objects on the order of 10–100 μm. Even higher resolution may be desirable in some embodiments, but with increase resolution, the time required to fully scan a substrate will increase; thus, in some embodiments a compromise may have to be made between speed and resolution. Increases in scanning time can be achieved by a system which only scans positions where microparticles are known to be located, e.g. from an initial full scan. Preferably, microparticle size and scanning system resolution are selected to permit resolution of fluorescently labeled microparticles randomly disposed on a plane at a density between about ten thousand to one hundred thousand microparticles per $cm^2$.

In sequencing applications, loaded microparticles can be fixed to the surface of a substrate in variety of ways. The fixation should be strong enough to allow the microparticles to undergo successive cycles of reagent exposure and washing without significant loss. When the substrate is glass, its surface may be derivatized with an alkylamino linker using commercially available reagents, e.g. Pierce Chemical, which in turn may be cross-linked to avidin, again using conventional chemistries, to form an avidinated surface. Biotin moieties can be introduced to the loaded microparticles in a number of ways. For example, a fraction, e.g. 10–15 percent, of the cloning vectors used to attach tags to polynucleotides are engineered to contain a unique restriction site (providing sticky ends on digestion) immediately adjacent to the polynucleotide insert at an end of the polynucleotide opposite of the tag. The site is excised with the polynucleotide and tag for loading onto microparticles'. After loading, about 10–15 percent of the loaded polynucleotides will possess the unique restriction site distal from the microparticle surface. After digestion with the associated restriction endonuclease, an appropriate double stranded adaptor containing a biotin moiety is ligated to the sticky end. The resulting microparticles are then spread on the avidinated glass surface where they become fixed via the biotin-avidin linkages.

Alternatively and preferably when sequencing by ligation is employed, in the initial ligation step a mixture of probes is applied to the loaded microparticle: a fraction of the probes contain a type IIs restriction recognition site, as required by the sequencing method, and a fraction of the probes have no such recognition site, but instead contain a biotin moiety at its non-ligating end. Preferably, the mixture comprises about 10–15 percent of the biotinylated probe.

Parallel Sequencing

The tagging system of the invention can be used with single base sequencing methods to sequence polynucleotides up to several kilobases in length. The tagging system permits many thousands of fragments of a target polynucleotide to be sorted onto one or more solid phase supports and sequenced simultaneously. In accordance with a preferred implementation of the method, a portion of each sorted fragment is sequenced in a stepwise fashion on each of the many thousands of loaded microparticles which are fixed to a common substrate-such as a microscope slide-associated with a scanning system, such as that described above. The size of the portion of the fragments sequenced depends of several factors, such as the number of fragments generated and sorted, the length of the target polynucleotide, the speed and accuracy of the single base method employed, the number of microparticles and/or discrete regions that may be monitored simultaneously; and the like. Preferably, from 12–50 bases are identified at each microparticle or region; and more preferably, 18–30 bases are identified at each microparticle or region. With this information, the sequence of the target polynucleotide is determined by collating the 12–50 base fragments via their overlapping regions, e.g. as described in U.S. Pat. No. 5,002,867. The following references provide additional guidance in determining the portion of the fragments that must be sequenced for successful reconstruction of a target polynucleotide of a given length: Drmanac et al., Genomics, 4:114–128 (1989); Bains, DNA Sequencing and Mapping, 4:143–150 (1993); Bains, Genomics, 11:294–301 (1991); Drmanac et al., J. Biomolecular Structure and Dynamics, 8:1085–1102 (1991); and Pevzner, J. Biomolecular Structure and Dynamics, 7:63–73 (1989). Preferably, the length of the target polynucleotide is between 1 kilobase and 50 kilobases. More preferably, the length is between 10 kilobases and 40 kilobases.

Fragments may be generated from a target polynucleotide in a variety of ways, including so-called "directed" approaches where one attempts to generate sets of fragments covering the target polynucleotide with minimal overlap, and so-called "shotgun" approaches where randomly overlapping fragments are generated. Preferably, "shotgun" approaches to fragment generation are employed because of their simplicity and inherent redundancy. For example, randomly overlapping fragments that cover a target polynucleotide are generated in the following conventional "shotgun" sequencing protocol, e.g. as disclosed in Sambrook et al. (cited above). As used herein, "cover" in this context means that every portion of the target polynucleotide sequence is represented in each size range, e.g. all fragments between 100 and 200 basepairs in length, of the generated fragments. Briefly, starting with a target polynucleotide as an insert in an appropriate cloning vector, e.g. λ, phage, the vector is expanded, purified and digested with the appropriate restriction enzymes to yield about 10–15 μg of purified insert. Typically, the protocol results in about 500–1000 subclones per microgram of starting DNA. The insert is separated from the vector fragments by preparative gel electrophoresis, removed from the gel by conventional methods, and resuspended in a standard buffer, such as TE (Tris-EDTA). The restriction enzymes selected to excise the insert from the vector preferably leave compatible sticky ends on the insert, so that the insert can be self-ligated in preparation for generating randomly overlapping fragments. As explained in Sambrook et al. (cited above), the circularized DNA yields a better random distribution of fragments than linear DNA in the fragmentation methods employed below. After self-ligating the insert, e.g. with T4 ligase using conventional protocols, the purified ligated insert is fragmented by a standard protocol, e.g. sonication or DNase I digestion in the presence of $Mn^{++}$. After fragmentation the ends of the fragments are repair, e.g. as described in Sambrook et al. (cited above), and the repaired fragments are separated by size using gel electrophoresis. Fragments in the 300–500 basepair range are selected and eluted from the gel by conventional means, and ligated into a tag-carrying vector as described above to form a library of tag-fragment conjugates.

As described below, a sample containing several thousand tag-fragment conjugates are taken from the library and expanded, after which the tag-fragment inserts are excised from the vector and prepared for specific hybridization to the tag complements on microparticles, as described above. Depending of the size of the target polynucleotide, multiple samples may be taken from the tag-fragment library and separately expanded, loaded onto microparticles and sequenced. The number of doubles selected will depend on the fraction of the tag repertoire represented in a sample. (The probability of obtaining triples—three different polynucleotides with the same tag—or above can safely be ignored). As mentioned above, the probability of doubles in a sample can be estimated from the Poisson distribution $p(double)=m^2 e^{-m}/2$, where m is the fraction of the tag repertoire in the sample. Table IV below lists probabilities of obtaining doubles in a sample for given tag size, sample size, and repertoire diversity.

TABLE IV

| Number of words in tag from 8 word set | Size of tag repertoire | Size of sample | Fraction of repertoire sampled | Probability of double |
| --- | --- | --- | --- | --- |
| 7 | $2.1 \times 10^6$ | 3000 | $1.43 \times 10^{-3}$ | $10^{-6}$ |
| 8 | $1.68 \times 10^7$ | $3 \times 10^4$ | $1.78 \times 10^{-3}$ | $1.6 \times 10^{-6}$ |
|   |   | 3000 | $1.78 \times 10^{-4}$ | $1.6 \times 10^{-8}$ |
| 9 | $1.34 \times 10^8$ | $3 \times 10^5$ | $2.24 \times 10^{-3}$ | $2.5 \times 10^{-6}$ |
|   |   | $3 \times 10^4$ | $2.24 \times 10^{-4}$ | $2.5 \times 10^{-8}$ |
| 10 | $1.07 \times 10^9$ | $3 \times 10^6$ | $2.8 \times 10^{-3}$ | $3.9 \times 10^{-6}$ |
|   |   | $3 \times 10^5$ | $2.8 \times 10^{-4}$ | $3.9 \times 10^{-8}$ |

In any case, the loaded microparticles are then dispersed and fixed onto a glass microscope slide, preferably via an avidin-biotin coupling. Preferably, at least 15–20 nucleotides of each of the random fragments are simultaneously sequenced with a single base method. The sequence of the target polynucleotide is then reconstructed by collating the partial sequences of the random fragments by way of their overlapping portions, using algorithms similar to those used for assembling contigs, or as developed for sequencing by hybridization, disclosed in the above references.

Kits for Implementing the Method of the Invention

The invention includes kits for carrying out the various embodiments of the invention. Preferably, kits of the invention include a repertoire of tag complements attached to a solid phase support. Additionally, kits of the invention may include the corresponding repertoire of tags, e.g. as primers for amplifying the polynucleotides to be sorted or as elements of cloning vectors which can aim be used to amplify the polynucleotides to be sorted. Preferably, the repertoire of tag complements are attached to microparticles. Kits may also contain appropriate buffers for enzymatic processing, detection chemistries, e.g. fluorescent or chemiluscent tags, and the like, instructions for use, processing enzymes, such as ligases, polymerases, transferases, and so on. In an important embodiment for sequencing, kits may also include substrates, such as a avidinated microscope slides, for fixing loaded microparticles for processing.

Example I

Sorting Multiple Target Polynucleotides Derived from pUC 19

A mixture of three target polynucleotide-tag conjugates are obtained as follows: First, the following six oligonucleotides are synthesized and combined pairwise to form tag 1, tag 2, and tag 3:

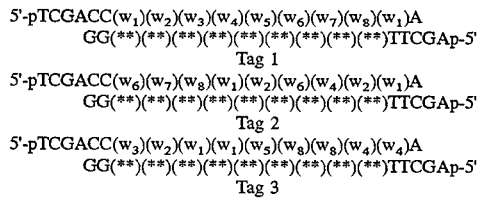

Tag 1

Tag 2

Tag 3 where "p" indicates a monophosphate, the $w_i$'s represent the subunits define in Table I, and the terms "(**)" represent their respective complements. A pUC 19 is digested with Sal I and Hind III, the large fragment is purified, and separately ligated with tags 1, 2, and 3, to form pUC 19-1, pUC 19-2, and pUG 19-3, respectively. The three recombinants are separately amplified and isolated, after which pUC19-1 is digested with Hind III and Aat I, pUC19-2 is digested with Hind III and Ssp I, and pUC19-3 is digested with lid El and Xmn I. The small fragments are isolated using conventional protocols to give three double stranded fragments about 250, 375, and 575 basepairs in length, respectively, and each having a recessed 3' strand adjacent to the tag and a blunt or 3' protruding strand at the opposite end. Approximately 12 moles of each fragment are mixed with 5 units T4 DNA polymerase in the manufacturer's recommended reaction buffer containing 33 μM deoxycytosine triphosphate. The reaction mixture is allowed to incubate at 37° C. for 30 minutes, after which the reaction is stopped by placing on ice. The fragments are then purified by conventional means.

CPG microparticles (37–74 mm particle size, 500 angstrom pore size, Pierce Chemical) are derivatized with the linker disclosed by Maskos and Southern, Nucleic Acids Research, 20:1679–1684 (1992). After separating into three aliquots, the complements of tags 1, 2, and 3 are synthesized on the microparticles using a conventional automated DNA synthesizer, e.g. a model 392 DNA synthesizer (Applied Biosystems, Foster City, CA). Approximately 1 mg of each of the differently derivatized microparticles are placed in separate vessels.

The T4 DNA polymerase-treated fragments excised from pUC 19-1, -2, and -3 are resuspended in 50 μL of the manufacturer's recommended buffer for Taq DNA ligase (New England Biolabs). The mixture is then equally divided among the three vessels containing the 1 mg each of derivatized CPG microparticles. 5 units of Taq DNA ligase is added to each vessel, after which they are incubated at 55° C. for 15 minutes. The reaction is stopped by placing on ice and the microparticles are washed several times by repeated centrifugation and resuspension in TE. Finally, the microparticles are resuspended in Nde I reaction buffer (New England Biolabs) where the attached polynucleotides are digested. After separation from the microparticles the polynucleotide fragments released by Nde I digestion are fluorescently labeled by incubating with Sequence DNA polymerase and fluorescein labeled thymidine triphosphate (Applied Biosystems, Foster City, CA). The fragments are then separately analyzed on a nondenaturing polyacrylamide gel using an Applied Biosystems model 373 DNA sequencer.

Example II

Parallel Sequencing of SV40 Fragments

A repertoire of 36-mer tags consisting of nine 4-nucleotide subunits selected from Table I is prepared by separately synthesizing tags and tag complements by a split and mix approach, as described above. The repertoire is synthesized so as to permit ligation into a Sma I/Hind III digested M13mp19. Thus, as in Example I, one set of oligonucleotides begins with the addition of A followed by nine rounds of split and mix synthesis wherein the oligonucleotide is extended subunit-wise by 3'-phosphoramidite derivatived 4-mers corresponding to the subunits of Table I. The synthesis is then completed with the nucleotide-by-nucleotide addition of one half of the Sma I recognition site (GGG), two G's, and a 5'-monophosphate, e.g. via the Phosphate-ON reagent available from Clontech Laboratories (Palo Alto, CA). The other set of oligonucleotides begins with the addition of three C's (portion of the Sma I recognition site) and two G's, followed by nine rounds of split and mix synthesis wherein the oligonucleotide is extended by 3'-phosphoramidite derivatized 4-mers corresponding to the complements of the subunits of Table I. Synthesis is completed by the nucleotide-by-nucleotide addition of the Hind III recognition site and a 5'-monophosphate. After separation from the synthesis supports the oligonucleotides are mixed under conditions that permit formation of the following duplexes:

5'-pGGGCC($w_i$) ($w_i$) ($w_i$) ($w_i$) ($w_i$) ($w_i$) ($w_i$) ($w_i$) ($w_i$)A

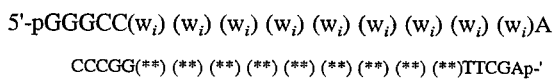

The mixture of duplexes is then ligated into a Sma I/Hind III-digested M13mp19. A repertoire of tag complements are synthesized on CPG microparticles as described above.

Next the following adaptor (SEQ ID NO: 2 and SEQ ID NO: 7) is prepared which contains a Fok I site and portions of Eco RI and Sma I sites:

```
5'-pAATTCGGATGATGCATGCATCGACCC
        GCCTACTACGTACGTAGCTGGGp-5'
  EcoRI      FokI          SmaI
```

The adaptor is ligated into the Eco RI/Sma I digested M13 described above.

Separately, SV40 DNA is fragmented by sonication following the protocol set forth in Sambrook et al. (cited above). The resulting fragments are repaired using standard protocols and separated by size. Fragments in the range of 300–500 basepairs are selected and ligated into the Sma I digested M13 described above to form a library of fragment-tag conjugates, which is then amplified. A sample containing several thousand different fragment-tag conjugates is taken from the library, further amplified, and the fragment-tag inserts are excised by digesting with Eco RI and Hind III. The excised fragment-tag conjugates are treated with T4 DNA polymerase in the presence of deoxycytidine triphosphate, as described in Example I, to expose the oligonucleotide tags for specific hybridization to the CPG microparticles.

After hybridization and ligation, as described in Example I, the loaded microparticles are treated with Fok I to produce a 4-nucleotide protruding strand of a predetermined sequence. A 10:1 mixture (probe 1: probe 2) of the following probes (SEQ ID NO: 3, SEQ ID NO: 8, SEQ ID NO: 9 and SEQ ID NO: 10) are ligated to the polynucleotides on microparticles.

```
Probe 1   FAM-    ATCGGATGAC
                  TAGCCTACTGAGCT
Probe 2   biotin- ATC ... AC
                  TAG ... TGAGCT
```

FAM represents a fluorescein dye attached to the 5'-hydroxyl of the top strand of Probe 1 through an aminophosphate linker available from Applied Biosystems. (Aminolinker). The biotin may also be attached through an Aminolinker moiety and optionally may be further extended via polyethylene oxide linkers, e.g. Jaschke et al. (cited above).

The loaded microparticles are then deposited on the surface of an avidinated glass slide to which and from which reagents and wash solutions can be delivered and removed. The avidinated slide with the attached microparticles is examined with a scanning fluorescent microscope (e.g. Zeiss Axioskop equipped with a Newport Model PM500-C motion controller, a Spectra-Physics Model 2020 argon ion laser producing a 488 nm excitation beam, and a 520 nm long-pass emission filter, or like apparatus). The excitation beam and fluorescent emissions are delivered and collected, respectively, through the same objective lens. The excitation beam and collected fluorescence are separated by a dichroic mirror which directs the collected fluorescence through a series of bandpass filters and to photon-counting devices corresponding to the fluorophors being monitored, e.g. comprising Hamamatsu model 9403-02 photomultipliers, a Stanford Research Systems model SR445 amplifier and model SR430 multichannel scaler, and digital computer, e.g. a 486-based computer. The computer generates a two dimensional map of the slide which registers the positions of the microparticles.

After cleavage with Fok I to remove the initial probe, the polynucleotides on the attached microparticles undergo 20 cycles of probe ligation, washing detection, cleavage, and washing, in accordance with the preferred single base sequencing methodology described below. Within each detection step, the scanning system records the fluorescent emission corresponding the base identified at each microparticle. Reactions and washes below are generally carried out with manufacturer's (New England Biolabs') recommended buffers for the enzymes employed, unless otherwise indicated. Standard buffers are also described in Sambrook et al. (cited above).

The following four sets of mixed probes (SEQ ID NO: 11, SEQ ID NO: 12, SEQ ID NO: 13, SEQ ID NO: 14, and SEQ ID NO: 15) are provided for addition to the target polynucleotides:

TAMRA-ATCGGATGACATCAAC TAGCCTACTGTAGT-
 -TGANNN

FAM-ATCGGATGACATCAAC TAGCCTACTGTAGTTGCNNN

ROX-ATCGGATGACATCAAC TAGCCTACTGTAGTTGGNNN

JOE-ATCGGATGACATCAAC TAGCCTACTGTAGTTGTNNN where TAMRA, FAM, ROX, and JOE are spectrally resolvable fluorescent labels attached by way of Aminolinker II (all being available from Applied Biosystems, Inc., Foster City, Calif.); the bold faced nucleotides are the recognition site for Fok I endonuclease, and "N" represents any one of the four nucleotides, A, C, G, T. TAMRA (tetramethylrhodamine), FAM (fluorescein), ROX (rhodamine X), and JOE (2',7'-dimethoxy-4',5'-dichlorofluorescein)and their attachment to oligonucleotides is also described in Fung et al., U.S. Pat. No. 4,855,225.

The above probes are incubated in approximately 5 molar excess of the target polynucleotide ends as follows: the probes are incubated for 60 minutes at 16° C. with 200 units of T4 DNA ligase and the anchored target polynucleotide in T4 DNA ligase buffer; after washing, the target polynucleotide is then incubated with 100 units T4 polynucleotide kinase in the manufacturer's recommended buffer for 30 minutes at 37° C., washed, and again incubated for 30 minutes at 16° C. with 200 units of T4 DNA ligase and the anchored target polynucleotide in T4 DNA ligase buffer. Washing is accomplished by successively flowing volumes of wash buffer over the slide, e.g. TIE, disclosed in Sambrook et al. (cited above). After the cycle of ligation-phosphorylation-ligation and a final washing, the attached microparticles are scanned for the presence of fluorescent label, the positions and characteristics of which are recorded by the scanning system. The labeled target polynucleotide, i.e. the ligated complex, is then incubated with 10 units of Fok I in the manufacturer's recommended buffer for 30 minutes at 37° C., followed by washing in TE. As a result the target polynucleotide is shortened by one nucleotide on each strand and is ready for the next cycle of ligation and cleavage. The process is continued until twenty nucleotides are identified.

APPENDIX I

Exemplary computer program for
generating minimally cross hybridizing sets

```
Program minxh
c
c
c
      integer*2 sub1(6),mset1(1000,6),mset2(1000,6)
      dimension nbase(6)
c
c
      write(*,*)'ENTER SUBUNIT LENGTH'
```

APPENDIX I-continued

Exemplary computer program for
generating minimally cross hybridizing sets

```
          read(*,100)nsub
100       format(i1)
          open(1,file='sub4.dat',form='formatted',status='new')
c
c
          nset=0
          do 7000 m1=1,3
            do 7000 m2=1,3
              do 7000 m3=1,3
                do 7000 m4=1,3
                  sub1(1)=m1
                  sub1(2)=m2
                  sub1(3)=m3
                  sub1(4)=m4
c
c
          ndiff=3
c
c
c         Generate set of subunits differing from
c         sub1 by at least ndiff nucleotides.
c         Save in mset1.
c
c
c
          jj=1
          do 900 j=1,nsub
900         mset1(1,j)=sub1(j)
c
c
          do 1000 k1=1,3
            do 1000 k2=1,3
              do 1000 k3=1,3
                do 1000 k4=1,3
c
c
                  nbase(1)=k1
                  nbase(2)=k2
                  nbase(3)=k3
                  nbase(4)=k4
c
                  n=0
                  do 1200 j=1,nsub
                    if(sub1(j).eq.1 .and. nbase(j).ne.1 .or.
        1            sub1(j).eq.2 .and. nbase(j).ne.2 .or.
        3            sub1(j).eq.3 .and. nbase(j).ne.3) then
                      n=n+1
                    endif
1200              continue
c
c
                  if(n.ge.ndiff) then
c
c
c                                       If number of mismatches
c                                       is greater than or equal
c                                       to ndiff then record
c                                       subunit in matrix mset
c
c
                    jj=jj+1
                    do 1100 i=1,nsub
1100                  mset1(jj,i)=nbase(i)
                  endif
c
c
1000      continue
c
c
          do 1325 j2=1,nsub
            mset2(1,j2)=mset1(1,j2)
1325        mset2(2,j2)=mset1(2,j2)
c
c
c
c                                       Compare subunit 2 from
c                                       mset1 with each successive
```

APPENDIX I-continued

Exemplary computer program for
generating minimally cross hybridizing sets

```
c                                       subunit in mset1, i.e. 3,
c                                       4,5, . . . etc. Save those
c                                       with mismatches .ge. ndiff
c                                       in matrix mset2 starting at
c                                       position 2.
c                                       Next transfer contents
c                                       of mset2 into mset1 and
c                                       start
c                                       comparisons again this time
c                                       starting with subunit 3.
c                                       Continue until all subunits
c                                       undergo the comparisons.
c
c
          npass=0
c
c
1700      continue
          kk=npass+2
          npass=npass+1
c
c
          do 1500 m=npass+2,jj
            n=0
            do 1600 j=1,nsub
              if(mset1(npass+1,j).eq.1.and.mset1(m,j).ne.1.or.
                 mset1(npass+1,j).eq.2.and.mset1(m,j).ne.2.or.
                 mset1(npass+1,j).eq.3.and.mset1(m,j).ne.3) then
                n=n+1
              endif
1600        continue
            if(n.ge.ndiff) then
              kk=kk+1
              do 1625 i=1,nsub
1625            mset2(kk,i)=mset1(m,i)
            endif
1500      continue
c
c
c                                       kk is the number of subunits
c                                       stored in mset2
c
c
c
c                                       Transfer contents of mset2
c                                       into mset1 for next pass.
c
          do 2000 k=1,kk
            do 2000 m=1,nsub
2000          mset1(k,m)=mset2(k,m)
          if(kk.lt.jj) then
            jj=kk
            goto 1700
          endif
c
c
          nset=nset+1
          write(1,7009)
7009      format(/)
          do 7008 k=1,kk
7008        write(1,7010)(mset1(k,m),m=1,nsub)
7010      format(4i1)
          write(*,*)
          write(*,120) kk,nset
120       format(1x,'Subunits in set=',i5,2x,'Set No=',i5)
7000      continue
          close(1)
c
c
          end
```

I claim:

1. A repertoire of oligonucleotide tags, wherein the oligonucleotide tags of the repertoire are of the form:

$$S_1 S_2 S_3 \ldots S_n$$

wherein each of $S_1$ through $S_n$ are subunits consisting of an oligonucleotide having a length from three to six nucleotides and being selected from a minimally cross-hybridizing set, wherein a subunit of the set and a complement of any other subunit of the set would have at least two mismatches; and n is in the range of from 4 to 10.

2. The repertoire of claim 1 wherein said subunits consist of an oligonucleotide having a length from four to five nucleotides and wherein n is in the range of from 6 to 9.

3. A repertoire of cloning vectors for attaching oligonucleotide tags to polynucleotides, wherein each of the vectors comprises a double stranded element corresponding to an oligonucleotide tag of the form:

$$S_1 S_2 S_3 \ldots S_n$$

wherein each of $S_1$ through $S_n$ are subunits consisting of an oligonuculeotide having a length from three to six nucleotides and being selected from a minimally cross-hybridizing set, wherein a subunit of the set and a complement of any other subunit of the set would have at least two mismatches; and n is in the range of from 4 to 10.

4. The repertoire of claim 3 wherein said double stranded element is adjacent to a polylinker region coming one or more restriction endonuclease cleavage sites for inserting said polynucleotides into said cloning vector.

* * * * *

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 38 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GAGGATGCCT TTATGGATCC ACTCGAGATC CCAATCCA                38
```

( 2 ) INFORMATION FOR SEQ ID NO: 2:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
AATTCGGATG ATGCATGCAT CGACCC                             26
```

( 2 ) INFORMATION FOR SEQ ID NO: 3:

( i ) SEQUENCE CHARACTERISTICS:
        ( A ) LENGTH: 14 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
TCGAGTCATC CGAT                                          14
```

( 2 ) INFORMATION FOR SEQ ID NO: 4:

( i ) SEQUENCE CHARACTERISTICS:
        ( A ) LENGTH: 16 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO: 4:

```
ATCGGATGAC ATCAAC                                        16
```

( 2 ) INFORMATION FOR SEQ ID NO: 5:

( i ) SEQUENCE CHARACTERISTICS:
        ( A ) LENGTH: 11 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
CTAGTCGACC A                                             11
```

( 2 ) INFORMATION FOR SEQ ID NO: 6:

( i ) SEQUENCE CHARACTERISTICS:
        ( A ) LENGTH: 11 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

NRRGATCYNN N    11

( 2 ) INFORMATION FOR SEQ ID NO: 7:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GGGTCGATGC ATGCATCATC CG    22

( 2 ) INFORMATION FOR SEQ ID NO: 8:

( i ) SEQUENCE CHARACTERISTICS:
        ( A ) LENGTH: 10 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 8:

ATCGGATGAC    10

( 2 ) INFORMATION FOR SEQ ID NO: 9:

( i ) SEQUENCE CHARACTERISTICS:
        ( A ) LENGTH: 10 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 9:

ATCNNNNNAC    10

( 2 ) INFORMATION FOR SEQ ID NO: 10:

( i ) SEQUENCE CHARACTERISTICS:
        ( A ) LENGTH: 14 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 10:

TCGAGTNNNN NGAT    14

( 2 ) INFORMATION FOR SEQ ID NO: 11:

( i ) SEQUENCE CHARACTERISTICS:
        ( A ) LENGTH: 16 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 11:

ATCGGATGAC ATCAAC    16

( 2 ) INFORMATION FOR SEQ ID NO: 12:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 12:

NNNAGTTGAT GTCATCCGAT    20

(2) INFORMATION FOR SEQ ID NO: 13:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 13:

NNNCGTTGAT GTCATCCGAT    20

(2) INFORMATION FOR SEQ ID NO: 14:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 14:

NNNGGTTGAT GTCATCCGAT    20

(2) INFORMATION FOR SEQ ID NO: 15:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 15:

NNNTGTTGAT GTCATCCGAT    20

(2) INFORMATION FOR SEQ ID NO: 16:

(i) SEQUENCE CHARACTERISTICS:
        (A) LENGTH: 37 nucleotides
        (B) TYPE: nucleic acid
        (C) STRANDEDNESS: double
        (D) TOPOLOGY: linear (xi) SEQUENCE DESCRIPTION: SEQ ID NO: 16:

NNNNNGGATG NNNNNNNNNN NNNTNNNNNN NNNNNNN    37